US012595229B2

(12) United States Patent
Harada

(10) Patent No.: US 12,595,229 B2
(45) Date of Patent: Apr. 7, 2026

(54) METHOD FOR PRODUCING DERIVATIVE OF ORGANIC SUBSTANCE AND METHOD FOR ANALYZING SAMPLE CONTAINING ORGANIC SUBSTANCE

(71) Applicant: Ajinomoto Co., Inc., Tokyo (JP)

(72) Inventor: Masashi Harada, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 986 days.

(21) Appl. No.: 17/700,721

(22) Filed: Mar. 22, 2022

(65) Prior Publication Data

US 2022/0267264 A1 Aug. 25, 2022

Related U.S. Application Data

(63) Continuation of application No. PCT/JP2020/036408, filed on Sep. 25, 2020.

(30) Foreign Application Priority Data

Sep. 26, 2019 (JP) ................................ 2019-176047

(51) Int. Cl.

*C07C 319/18* (2006.01)
*C07C 315/00* (2006.01)
*C07C 319/20* (2006.01)
*C07D 207/416* (2006.01)
*G01N 30/06* (2006.01)

(52) U.S. Cl.

CPC .......... *C07C 319/18* (2013.01); *C07C 315/00* (2013.01); *C07C 319/20* (2013.01); *C07D 207/416* (2013.01); *G01N 30/06* (2013.01)

(58) Field of Classification Search

None
See application file for complete search history.

(56) References Cited

U.S. PATENT DOCUMENTS

| | | | |
|---|---|---|---|
| 4,316,906 | A | 2/1982 | Ondetti et al. |
| 4,914,226 | A | 4/1990 | Di Trapani et al. |
| 2015/0064797 | A1 | 3/2015 | Mita et al. |
| 2019/0041384 | A1 | 2/2019 | Haxo et al. |

FOREIGN PATENT DOCUMENTS

| | | |
|---|---|---|
| JP | 63-23834 A | 2/1988 |
| JP | 2015-49201 | 3/2015 |
| JP | 2019-517005 | 6/2019 |

OTHER PUBLICATIONS

International Search Report in PCT/JP2020/036408 issued Dec. 1, 2020.
Bansal, Getti et al., "Imparting mineral affinity to proteins with thiol-labile disulfide linkages", Journal of Biomedical Materials Research, Part A, 2005, 74A(4), pp. 618-628.
Zhang, Sufeng et al., "Cleavage of disulfide-linked fetuin-bisphosphonate conjugates with three physiological thiols", Biomacromolecules, 2005, 6(5), pp. 2800-2808.
De Lucchi, Ottorino et al., "1,1-Bis(phenylsulfonyl)ethylene", e-EROS Encyclopedia of Reagents for Organic Synthesis, 2007, pp. 1-3.
Hea Jin Park et al., "Validation of high-performance liquid chromatography-boron-doped diamond detection for assessing hepatic glutathione redox status" Anal.Biochem.,407(2010)151-159.
Abad Khan et al., "A new HPLC method for the simultaneous determination of ascorbic acid and aminothiols in human plasma and erythrocytes using electrochemical detection" Talanta, 84(2011)789-801.
Frank Tietze, "Enzymic Method for Quantitative Determination of Nanogram Amounts of Total and Oxidized Glutathione: Applications to Mammalian Blood and Other Tissues" Anal. Biochem.,27(1969)502-522.
Tomofumi Santa et al., "Suppression of thiol exchange reaction in the determination of reduced-form thiols by high-performance liquid chromatography with fluorescence detection after derivatization with fluorogenic benzofurazan reagent, 7-fluoro-2,1,3-benzoxadiazole-4-sulfonate and 4-aminosulfonyl-7-fluoro-2,1,3-benzoxadiazole", Biomed.Chromatogr.,20(2006)656-661.
V. Cavrini et al., "1,1'-[Ethenylidenebis(Sulfonyl)]Bis-Benzene: A Useful Pre-Chromatographic Derivatization Reagent for HPLC Analyses of Thioi Drugs", Chromatographia(1996)42:515.
Roberto Gotti et al., "Analytical study of penicillamine in pharmaceuticals by capillary zone electrophoresis", Journal of Chromatography A, vol. 844, Issues1-2, Jun. 4, 1999, pp. 361-369.
Ping Liu et al., "Determination of thiol metabolites in human urine by stable isotope labeling in combination with pseudo-targeted mass spectrometry analysis", Sci Rep.6(2016)21433.
Lei Yang et al. , "A Triple-Emission Fluorescent Probe for Discriminatory Detection of Cysteine/Homocysteine, Glutathione/Hydrogen Sulfide, and Thiophenol in Living Cells", J Chromatogr B Analyt Technol Biomed Life Sci,1083(2018)12-19.
Theodor Wieland et al., "A base-cleavable protecting group for the cysteine sulfur" European Journal of Organic Chemistry, vol. 722, Issue 1, May 14, 1969, pp. 222-224.
Maria C. Aversa et al., "2,2-Bis(phenylsulfonyl)ethyl sulfides as efficient precursors of sulfenic acids" ARKIVOC 2009(viii)187-198.
Owen W. Griffith, "Determination of Glutathione and Glutathione Disulfide Using Glutathione Reductase and 2-Vinylpyridine", Analytical Biochemistry 106,207-212 (1980).

*Primary Examiner* — John S Kenyon
(74) *Attorney, Agent, or Firm* — Oblon, McClelland, Maier & Neustadt, L.L.P.

(57) ABSTRACT

Derivatives of an organic substance containing one or more groups selected from the group consisting of sulfanyl, selanyl and sulfino may be produced by reacting an organic substance containing one or more groups selected from the group consisting of sulfanyl, selanyl and sulfino with an olefin compound containing an ethylene structure having at least two electron-withdrawing groups except halogen atoms under an acidic condition to form a derivative of the organic substance.

14 Claims, 13 Drawing Sheets

METHOD FOR PRODUCING DERIVATIVE OF ORGANIC SUBSTANCE AND METHOD FOR ANALYZING SAMPLE CONTAINING ORGANIC SUBSTANCE

CROSS REFERENCES TO RELATED APPLICATIONS

This application is a continuation of International Patent Application No. PCT/JP2020/036408, filed on Sep. 25, 2020, and claims priority to Japanese Patent Application No. 2019-176047, filed on Sep. 26, 2019, both of which are incorporated herein by reference in their entireties.

BACKGROUND OF THE INVENTION

Field of the Invention

The present invention relates to methods for producing a derivative of an organic substance and to methods for analyzing a sample containing an organic substance.

Discussion of the Background

In living bodies, thiols play important roles such as, for example, to maintain the redox state in the body, to control protein functions, and to detoxify xenobiotic substances such as heavy metals.

Thus, attempts have been made in which thiols in samples such as biological samples are analyzed.

In exemplary techniques, thiols are analyzed with an electrochemical detector using redox reactions on the electrode surface (see Anal. Biochem., 407 (2010) 151-159 and Talanta, 84 (2011) 789-801, which are incorporated herein by reference in their entireties). Furthermore, attempts have been made in which thiols are converted into derivatives before analysis (see Anal. Biochem., 27 (1969) 502-522; Biomed. Chromatogr., 20 (2006) 656-661; Chromatographia (1996) 42: 515; Journal of Chromatography A, Volume 844, Issues 1-2, 4 Jun. 1999, Pages 361-369; Sci Rep, 6 (2016) 21433; and J Chromatogr B Analyt Technol Biomed Life Sci, 1083 (2018) 12-19, which are incorporated herein by reference in their entireties).

Thiols are known to react with carbon-carbon double bonds (see European Journal of Organic Chemistry, Volume 722, Issue 1, 14. May 1969, Pages 222-224 and ARKIVOC 2009 (viii) 187-198, which are incorporated herein by reference in their entireties).

SUMMARY OF THE INVENTION

The analysis methods of Anal. Biochem., 407 (2010) 151-159 and Talanta, 84 (2011) 789-801 analyze a thiol without derivatization. Thus, the thiol tends to be oxidized by dissolved oxygen present in, for example, the sample or an eluent used in the analysis, and consequently stable analytical results are difficult to obtain. Furthermore, electrochemical detectors do not have sufficient selectivity for thiols, and the measurement is sometimes interfered by contaminants present in samples such as amino acids, sugars and other complex contaminants. Furthermore, electrochemical detectors require maintenance such as cleaning of electrodes, and easily change the detection sensitivity and become unstable during use, thus causing difficulties in handling.

In the techniques of Anal. Biochem., 27 (1969) 502-522; Biomed. Chromatogr., 20 (2006) 656-661; Chromatographia (1996) 42: 515; and Journal of Chromatography A, Volume 844, Issues 1-2, 4 Jun. 1999, Pages 361-369, thiols are derivatized under neutral to basic conditions.

However, the present inventor has found that thiols are difficult to analyze because thiols are easily oxidized and easily undergo exchange reaction with disulfide compounds under neutral to basic conditions. Thus, it is difficult to analyze thiols accurately by the techniques of Anal. Biochem., 27 (1969) 502-522; Biomed. Chromatogr., 20 (2006) 656-661; Chromatographia (1996) 42: 515; and Journal of Chromatography A, Volume 844, Issues 1-2, 4 Jun. 1999, Pages 361-369 that involve the derivatization of thiols under neutral to basic conditions.

On the other hand, the techniques of Sci Rep, 6 (2016) 21433 and J Chromatogr B Analyt Technol Biomed Life Sci, 1083 (2018) 12-19 adopt acidic conditions (pH 3.5) for the derivatization of thiols. However, the reactivity is low and the reaction requires special conditions such as long reaction time or microwave irradiation.

Accordingly, it is an object of the present invention to provide methods for analyzing a sample containing an organic substance which do not suffer from the above-mentioned drawbacks.

This and other objects, which will become apparent during the following detailed description, have been achieved by the inventor's discovery that a derivative of an organic substance obtained by reacting a specific olefin compound with an organic substance containing one or more kinds of groups selected from the group consisting of sulfanyl, selanyl and sulfino under an acidic condition, is useful for analysis of the organic substance containing one or more kinds of groups selected from the group consisting of sulfanyl, selanyl and sulfino.

The techniques discussed above do not teach or suggest that (a) an olefin compound specified herein is reacted with an organic substance containing one or more kinds of groups selected from the group consisting of sulfanyl, selanyl and sulfino under an acidic condition, or that (b) a derivative of an organic substance obtained by the above reaction is useful for analysis of the organic substance containing one or more kinds of groups selected from the group consisting of sulfanyl, selanyl and sulfino.

Specifically, the present invention provides the following.

(1) A method for producing a derivative of an organic substance, the method comprising reacting an organic substance containing one or more kinds of groups selected from the group consisting of sulfanyl, selanyl and sulfino with an olefin compound under an acidic condition to form a derivative of the organic substance, wherein the olefin compound contains an ethylene structure having at least two electron-withdrawing groups except halogen atoms.

(2) The method for producing a derivative according to (1), wherein the ethylene structure has two of the electron-withdrawing groups.

(3) The method for producing a derivative according to (1) or (2), wherein two of the electron-withdrawing groups are bonded to a single carbon atom constituting the ethylene structure.

(4) The method for producing a derivative according to any one of (1) to (3), wherein the at least two electron-withdrawing groups are identical groups.

(5) The method for producing a derivative according to any one of (1) to (4), wherein the olefin compound is a compound represented by the following formula (I):

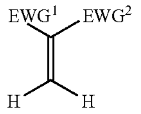

(I)

wherein $EWG^1$ and $EWG^2$ each independently indicate the electron-withdrawing group, and optionally form a ring together with the carbon atom to which $EWG^1$ and $EWG^2$ are bonded.

(6) The method for producing a derivative according to any one of (1) to (5), wherein the electron-withdrawing groups, or $EWG^1$ and $EWG^2$ are each independently —C(═O)—$OR^1$, —S(═O)$_2$—$R^2$, —P(═O)(—$OR^3$)$_2$, cyano, a halogen atom-substituted alkyl, carboxy, nitro, —S(═O)—$R^4$, —C(═O)—R, or —C(═O)—$NR^6R^7$, wherein $R^1$, $R^2$, $R^3$ and $R^4$ each independently indicate a monovalent hydrocarbon group or a monovalent heterocyclic group and optionally each have a substituent, and $R^5$, $R^6$ and $R^7$ each independently indicate a hydrogen atom, a monovalent hydrocarbon group or a monovalent heterocyclic group and optionally each have a substituent.

(7) The method for producing a derivative according to any one of (1) to (6), wherein the acidic condition is a condition at which pH is less than 6.0.

(8) The method for producing a derivative according to any one of (1) to (7), wherein the organic substance is one or more selected from the group consisting of cysteine, reduced glutathione, γ-glutamylcysteine, cysteinylglycine, homocysteine, N-acetylcysteine, cysteine persulfide, hypotaurine, glutathione persulfide and peptidic compounds containing a cysteine residue.

(9) The method for producing a derivative according to any one of (1) to (8), wherein the organic substance further contains an amino group, and the method comprises reacting the organic substance with the olefin compound under the acidic condition and subsequently performing reaction under a neutral or basic condition to form a derivative of the organic substance.

(10) A method for analyzing a sample containing an organic substance, the method comprising:

(1) mixing a sample containing an organic substance containing one or more kinds of groups selected from the group consisting of sulfanyl, selanyl and sulfino, and an olefin compound containing an ethylene structure having at least two electron-withdrawing groups except halogen atoms under an acidic condition to form a treated sample containing a derivative of the organic substance; and (2) analyzing the derivative of the organic substance in the treated sample.

(11) The method for analyzing a sample containing an organic substance according to (10), wherein the analyzing at (2) comprises:

(2a) separating the derivative of the organic substance from the treated sample, and (2b) detecting the derivative of the organic substance separated.

(12) The method for analyzing a sample containing an organic substance according to (10) or (11), wherein the sample further contains a disulfide compound.

(13) The method for analyzing a sample containing an organic substance according to (12), wherein the disulfide compound is one or more selected from the group consisting of oxidized glutathione and cystine.

(14) The method for analyzing a sample containing an organic substance according to any one of (10) to (13), wherein the organic substance further contains an amino group, and the mixing at (1) comprises (1') mixing the sample with the olefin compound under the acidic condition and subsequently performing mixing under a neutral or basic condition to form a treated sample containing a derivative of the organic substance.

(15) A derivatizing agent for derivatizing an organic substance containing one or more kinds of groups selected from the group consisting of sulfanyl, selanyl and sulfino under an acidic condition, the derivatizing agent comprising an olefin compound containing an ethylene structure having at least two electron-withdrawing groups except halogen atoms.

(16) A reagent for analyzing an organic substance containing one or more kinds of groups selected from the group consisting of sulfanyl, selanyl and sulfino, the reagent comprising the derivatizing agent according to (15).

Effect of the Invention

The present invention provides a novel method for producing a derivative of an organic substance containing one or more kinds of groups selected from the group consisting of sulfanyl (—SH), selanyl (—SeH) and sulfino (—S(═O)—OH); and a novel method for analyzing a sample containing such an organic substance.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
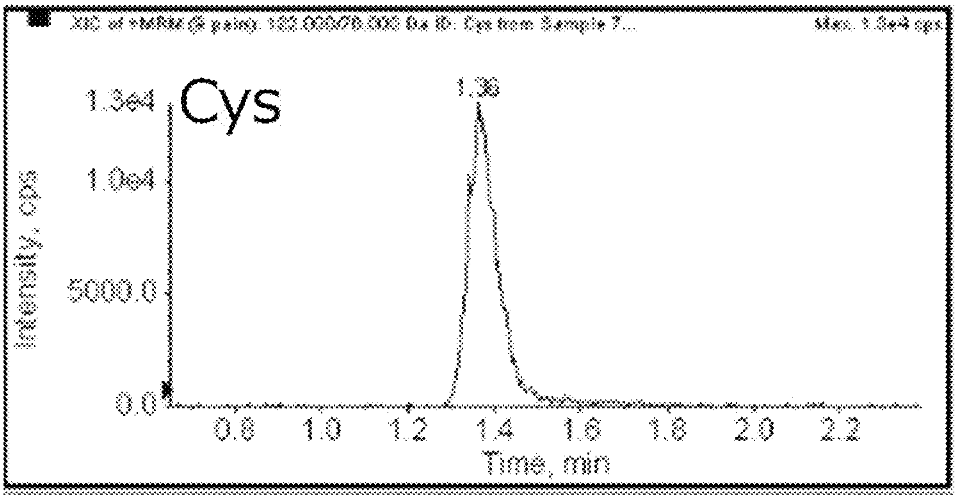
FIG. 1 is an exemplary chromatogram illustrating a peak of cysteine.

The present invention will be described in detail hereinbelow by illustrating embodiments and examples. However, it should be construed that the scope of the present invention is not limited to those embodiments and examples illustrated below. Furthermore, the term “agent” may mean a single substance or a composition composed of two or more kinds of substances.

1. Methods for Producing Derivatives of Organic Substances

An embodiment of the present invention resides in a method for producing a derivative of an organic substance that comprises reacting an organic substance containing one or more kinds of groups selected from the group consisting of sulfanyl, selanyl and sulfino with an olefin compound under an acidic condition to form a derivative of the organic substance.

Here, the olefin compound contains an ethylene structure having at least two electron-withdrawing groups except halogen atoms.

1.1. Organic Substances

An organic substance contains one or more kinds of groups selected from the group consisting of sulfanyl, selanyl and sulfino, preferably contains one or more kinds of groups selected from the group consisting of sulfanyl and sulfino, and more preferably contains sulfanyl. Here, the sulfanyl is a group represented by $-(S)_n-SH$, the selanyl is a group represented by —SeH, and the sulfino is a group represented by —(S=O)—OH.

Hereinbelow, “one or more kinds of groups selected from the group consisting of sulfanyl, selanyl and sulfino” may be referred to as the “group(s) A”.

In the present invention, sulfanyl is a group represented by $-(S)_n-SH$ (n represents an integer of 0 or greater).

By the derivative production method according to the present embodiment, even an organic substance having a group represented by $-(S)_n-SH$ (wherein n is an integer of 1 or greater) such as —S—SH or —S—S—SH (hereinafter, such an organic substance will be also referred to as a persulfide) can be derivatized with an olefin compound. Such persulfides (for example, cysteine persulfide) have an important role associated with the redox in living bodies. The derivative production method according to the present embodiment can derivatize a persulfide while maintaining the redox state thereof and thus enables one to grasp the redox state in the living body. From points of view such as the great varieties and abundance of sulfanyl-containing organic substances (in particular, natural organic substances in biological samples such as blood, saliva, urine and feces), the letter n in the group represented by $-(S)_n-SH$ is preferably 0, 1, 2 or 3, more preferably 0, 1 or 2, still more preferably 0 or 1, and particularly preferably 0.

In the present invention, selanyl is a group represented by —SeH. Selenium atom is a Group 16 atom in the periodic table similar to sulfur atom, and exhibits similar reactivity as sulfur atom. That is, the reactivity of a selenium atom in an organic substance with respect to an olefin compound is similar to the reactivity of a sulfur atom in an organic substance with respect to that olefin compound. Thus, an olefin compound with an ethylene structure that will be described later can react favorably with a sulfur atom in an organic substance and can also react favorably with a selenium atom in an organic substance.

The molecule of the organic substance may contain a plurality of groups belonging to one or more kinds of groups selected from the group consisting of sulfanyl, selanyl and sulfino (—S(=O)—OH).

The organic substance may have one or more (for example, two, three or four) functional groups in addition to the one or more kinds of groups selected from the group consisting of sulfanyl, selanyl and sulfino.

Examples of the functional groups include, but are not particularly limited to, hydroxy, carboxy, amino, alkylamino, dialkylamino, alkyloxy, alkyloxycarbonyl, alkylcarbonyl and alkylcarbonyloxy.

In an embodiment, the organic substance may contain an amino group in addition to the group A. Here, the amino groups that may be contained in the organic substances together with the groups A include, besides unsubstituted amino group ($-NH_2$), monosubstituted amino groups and disubstituted amino groups. The amino group that may be contained in the organic substance together with the group A is preferably one or more kinds of groups selected from the group consisting of an unsubstituted amino group and monosubstituted amino groups, and is more preferably an unsubstituted amino group. The organic substance containing the group(s) A may contain only one amino group or a plurality of amino groups in the molecule. The number of amino groups contained in the molecule of the organic substance may be 1, 2 or 3, preferably 1 or 2, and more preferably 1.

The organic substance may be one derived from a sample described later.

The organic substance may be a high-molecular compound or a low-molecular compound. The organic substance is preferably a low-molecular compound.

The low-molecular compound is a compound having a molecular weight of 1,500 or less. The molecular weight of the low-molecular compound may be 1,200 or less, 1,000 or less, 900 or less, 800 or less, 700 or less, 600 or less, 500 or less, 400 or less, or 300 or less. The molecular weight of the low-molecular compound may be 30 or more, 40 or more, or 50 or more.

The low-molecular compound may be an amino acid (for example, cysteine or selenocysteine), a peptidic compound or a salt of any of these compounds.

Here, the peptidic compound is a compound that has a structure resulting from the condensation of two or more molecules of amino acids.

The organic substance may be a high-molecular peptidic compound. Examples of the high-molecular peptidic compounds include proteins such as albumin.

The organic substance may be a natural compound or a synthetic compound.

Specific examples of the organic substances include cysteine, reduced glutathione, γ-glutamylcysteine, cysteinylglycine, homocysteine, N-acetylcysteine, cysteine persulfide (for example, S-mercaptocysteine, S-disulfanylcysteine, and S-trisulfanylcysteine), hypotaurine, glutathione persulfide, peptidic compounds containing a cysteine residue, allylmercaptan, 2-furfurylthiol, 3-mercapto-3-methylbutyl formate, 3-sulfanyl-1-hexanol, thiophen-2-ylmethanethiol, 1,6- hexanedithiol, 4-methyl-4-sulfanylpentan-2-one, 3-sulfanylpentan-2-one, thioterpineol and 4-methoxy-2-methylbutane-2-thiol.

The organic substances may be used singly, or two or more may be used in combination.

The organic substance is preferably one or more selected from the group consisting of cysteine, reduced glutathione, γ-glutamylcysteine, cysteinylglycine, homocysteine, N-acetylcysteine, cysteine persulfide (for example, S-mercaptocysteine, S-disulfanylcysteine, and S-trisulfanylcysteine), hypotaurine, glutathione persulfide and peptidic compounds containing a cysteine residue.

Here, the peptidic compounds containing a cysteine residue may be low-molecular compounds (for example, oligopeptides) or high-molecular compounds (for example, proteins).

1.2. Olefin Compounds

An olefin compound is a compound that includes an ethylene structure (an ethene structure) having at least two electron-withdrawing groups and is capable of reacting with the sulfanyl, selanyl or sulfino in the organic substance via the ethylene structure. In the present specification, the electron-withdrawing groups do not include halogen atoms.

The number of electron-withdrawing groups present in the ethylene structure is usually 2 or more and usually 4 or less, is preferably 2 or more and 3 or less, and is more preferably 2. When the number of electron-withdrawing groups is in the above range, the reactivity between the olefin compound and the organic substance is enhanced.

The electron-withdrawing groups may be monovalent or divalent.

The number of electron-withdrawing groups present in the ethylene structure means the number of bonds between the ethylene structure and the electron-withdrawing groups. That is, when an electron-withdrawing group is divalent, and bonded to one ethylene structure through the two bonds, the number of the electron-withdrawing groups present in the ethylene structure may be two.

The olefin compound is preferably such that two electron-withdrawing groups are bonded to a single carbon atom constituting the ethylene structure. In this case, the ethylene structure can attain enhanced reactivity at the carbon atom other than the carbon atom to which the two electron-withdrawing groups are bonded.

When two electron-withdrawing groups are bonded to a single carbon atom in the ethylene structure, or when an electron-withdrawing group is bonded to each of the adjacent carbon atoms in the ethylene structure, the two electron-withdrawing groups may form a ring together with the carbon atom or the carbon atoms to which they are bonded.

The olefin compound is preferably such that at least two of the electron-withdrawing groups present in the ethylene structure are identical groups.

The olefin compound is more preferably such that at least two of the electron-withdrawing groups present in the ethylene structure are identical groups, and that the two identical electron-withdrawing groups are bonded to a single carbon atom constituting the ethylene structure.

The olefin compound is still more preferably such that the ethylene structure has two identical electron-withdrawing groups, that the two identical electron-withdrawing groups are bonded to a single carbon atom constituting the ethylene structure, and that two identical groups (that may be hydrogen atoms) are bonded to the carbon atom other than the carbon atom to which the two electron-withdrawing groups are bonded.

This configuration can prevent the organic substance from being converted into a pair of diastereomers by the reaction between the olefin compound and the organic substance.

The ethylene structure may have a group that is not an electron-withdrawing group.

Examples of the groups that may be present in the ethylene structure and are not electron-withdrawing groups include monovalent hydrocarbon groups. This additional group is preferably one or more selected from the group consisting of monovalent chain hydrocarbons and monovalent aromatic hydrocarbon groups, and is more preferably one or more selected from the group consisting of alkyls and aryls.

Preferably, the ethylene structure has no groups other than the electron-withdrawing groups.

Examples of the electron-withdrawing groups include, but are not particularly limited to, $-C(=O)-OR^1$, $-S(=O)_2-R^2$, $-P(=O)(-OR^3)_2$, cyano, halogen atom-substituted alkyls (for example, perfluoroalkyls such as trifluoromethyl, and perchloroalkyls such as trichloromethyl), carboxy, nitro, $-S(=O)-R^4$, $-C(=O)-R^5$ and $-C(=O)-NR^6R^7$.

Here, $R^1$, $R^2$, $R^3$ and $R^4$ each independently indicate a monovalent hydrocarbon group or a monovalent heterocyclic group, and may or may not each have a substituent.

$R^5$, $R^6$ and $R^7$ each independently indicate a hydrogen atom, a monovalent hydrocarbon group or a monovalent heterocyclic group, and may or may not each have a substituent.

Examples of the monovalent hydrocarbon groups include monovalent chain hydrocarbon groups, monovalent alicyclic hydrocarbon groups and monovalent aromatic hydrocarbon groups.

The monovalent chain hydrocarbon groups mean hydrocarbon groups that are composed solely of a chain structure and do not contain a cyclic structure in the main chain. The chain structure may be linear or branched. Examples of the monovalent chain hydrocarbon groups include alkyls, alkenyls and alkynyls. The alkyls, the alkenyls and the alkynyls may be linear or branched.

The alkyls are preferably alkyls having a carbon number of 1 to 12, more preferably alkyls having a carbon number of 1 to 6, and still more preferably alkyls having a carbon number of 1 to 4. The number of carbon atoms does not include the number of carbon atoms in any substituents. Examples of the alkyls having a carbon number of 1 to 12 include methyl, ethyl, n-propyl, i-propyl, n-butyl, s-butyl, isobutyl, t-butyl, pentyl, hexyl, heptyl, octyl, nonyl, decyl and dodecyl.

The alkenyls are preferably alkenyls having a carbon number of 2 to 12, more preferably alkenyls having a carbon number of 2 to 6, and still more preferably alkenyls having a carbon number of 2 to 4. The number of carbon atoms does not include the number of carbon atoms in any substituents. Examples of the alkenyls having a carbon number of 2 to 12 include vinyl, propenyl and n-butenyl.

The alkynyls are preferably alkynyls having a carbon number of 2 to 12, more preferably alkynyls having a carbon number of 2 to 6, and still more preferably alkynyls having a carbon number of 2 to 4. The number of carbon atoms does not include the number of carbon atoms in any substituents. Examples of the alkynyls having a carbon number of 2 to 12 include ethynyl, propynyl and n-butynyl.

The alkyls are preferable as the monovalent chain hydrocarbon groups.

The monovalent alicyclic hydrocarbon groups mean hydrocarbon groups that contain only an alicyclic hydrocarbon as a ring structure and do not contain an aromatic ring, and the alicyclic hydrocarbon may be monocyclic or polycyclic. However, the monovalent alicyclic hydrocarbon groups are not necessarily composed solely of an alicyclic hydrocarbon and may contain a partial chain structure. Examples of the monovalent alicyclic hydrocarbon groups include cycloalkyls, cycloalkenyls and cycloalkynyls wherein these groups may be each monocyclic or polycyclic.

The cycloalkyls are preferably cycloalkyls having a carbon number of 3 to 12, more preferably cycloalkyls having a carbon number of 3 to 6, and still more preferably cycloalkyls having a carbon number of 5 to 6. The number of carbon atoms does not include the number of carbon atoms in any substituents. Examples of the cycloalkyls having a carbon number of 3 to 12 include cyclopropyl, cyclobutyl, cyclopentyl and cyclohexyl.

The cycloalkenyls are preferably cycloalkenyls having a carbon number of 3 to 12, more preferably cycloalkenyls having a carbon number of 3 to 6, and still more preferably cycloalkenyls having a carbon number of 5 to 6. The number of carbon atoms does not include the number of carbon atoms in any substituents. Examples of the cycloalkenyls having a carbon number of 3 to 12 include cyclopropenyl, cyclobutenyl, cyclopentenyl and cyclohexenyl.

The cycloalkynyls are preferably cycloalkynyls having a carbon number of 3 to 12, more preferably cycloalkynyls having a carbon number of 3 to 6, and still more preferably cycloalkynyls having a carbon number of 5 to 6. The number of carbon atoms does not include the number of carbon atoms in any substituents. Examples of the cycloalkynyls having a carbon number of 3 to 12 include cyclopropynyl, cyclobutynyl, cyclopentynyl and cyclohexynyl.

The cycloalkyls are preferable as the monovalent alicyclic hydrocarbon groups.

The monovalent aromatic hydrocarbon groups mean hydrocarbon groups that contain an aromatic ring structure. However, the monovalent aromatic hydrocarbon groups are not necessarily composed solely of an aromatic ring and may contain a partial structure such as a chain structure or an alicyclic hydrocarbon structure. That is, the monovalent aromatic hydrocarbon groups may be aralkyls. The aromatic ring may be monocyclic or polycyclic. The monovalent aromatic hydrocarbon groups are preferably aryls having a carbon number of 6 to 12, more preferably aryls having a carbon number of 6 to 10, and still more preferably aryls having a carbon number of 6. The number of carbon atoms does not include the number of carbon atoms in any substituents. Examples of the aryls having a carbon number of 6 to 12 include phenyl and naphthyl.

Phenyl is preferable as the monovalent aromatic hydrocarbon group.

Among these monovalent hydrocarbon groups described above, alkyls, cycloalkyls and aryls are preferable, and alkyls and aryls are more preferable.

The monovalent heterocyclic groups are groups that are derived from cyclic compounds containing a heterocyclic ring by the removal of one hydrogen atom therefrom. The heterocyclic group preferably includes one or more kinds of heteroatoms selected from the group consisting of an oxygen atom, a sulfur atom, a nitrogen atom, a phosphorus atom, a boron atom and a silicon atom, and more preferably includes one or more kinds of heteroatoms selected from the group consisting of an oxygen atom, a sulfur atom and a nitrogen atom. The monovalent heterocyclic groups are monovalent aromatic heterocyclic groups or monovalent nonaromatic heterocyclic groups.

The monovalent aromatic heterocyclic groups mean heterocyclic groups that contain a ring having aromaticity. The monovalent aromatic heterocyclic groups are preferably aromatic heterocyclic groups having a carbon number of 1 to 15, more preferably aromatic heterocyclic groups having a carbon number of 1 to 9, and still more preferably aromatic heterocyclic groups having a carbon number of 1 to 6. The number of carbon atoms does not include the number of carbon atoms in any substituents. Examples of the monovalent aromatic heterocyclic groups include pyrrolyl, furanyl, thiophenyl, pyridinyl, pyridazinyl, pyrimidinyl, pyrazinyl, triazinyl, pyrazolyl, imidazolyl, thiazolyl, isothiazolyl, oxazolyl, isoxazolyl, triazolyl, tetrazolyl, indolyl, purinyl, anthraquinolyl, carbazolyl, fluorenyl, quinolinyl, isoquinolinyl, quinazolinyl, acridinyl, coumarinyl, xanthenyl and phthalazinyl.

The monovalent nonaromatic heterocyclic groups mean heterocyclic groups that do not contain a ring having aromaticity. The monovalent nonaromatic heterocyclic groups are preferably nonaromatic heterocyclic groups having a carbon number of 2 to 15, more preferably nonaromatic heterocyclic groups having a carbon number of 2 to 9, and still more preferably nonaromatic heterocyclic groups having a carbon number of 2 to 6. The number of carbon atoms does not include the number of carbon atoms in any substituents. Examples of the monovalent nonaromatic heterocyclic groups include oxiranyl, aziridinyl, azetidinyl, oxetanyl, thietanyl, pyrrolidinyl, dihydrofuranyl, tetrahydrofuranyl, dioxolanyl, tetrahydrothiophenyl, pyrrolinyl, imidazolidinyl, oxazolidinyl, piperidinyl, dihydropyranyl, tetrahydropyranyl, tetrahydrothiopyranyl, morpholinyl, thiomorpholinyl, piperazinyl, dihydroxazinyl, tetrahydroxazinyl, dihydropyrimidinyl and tetrahydropyrimidinyl.

Among these monovalent heterocyclic groups, 5-membered or 6-membered heterocyclic groups are preferable.

Examples of the substituents include:

monovalent hydrocarbon groups (optionally further substituted with a halogen atom), monovalent heterocyclic groups (optionally further substituted with a halogen atom), —O—$R^{s1}$ (wherein $R^{s1}$ indicates a hydrogen atom or a monovalent hydrocarbon group), —(C═O)—$R^{s2}$ (wherein $R^{s2}$ indicates a hydrogen atom or a monovalent hydrocarbon group), —(C═O)—O—$R^{s3}$ (wherein $R^{s3}$ indicates a hydrogen atom or a monovalent hydrocarbon group), —O—(C═O)—$R^{s4}$ (wherein $R^{s4}$ indicates a hydrogen atom or a monovalent hydrocarbon group), —$N(R^{s5})_2$ (wherein $R^{s5}$ independently at each occurrence indicates a hydrogen atom or a monovalent hydrocarbon group), —(C═O)—$N(R^{s6})_2$ (wherein $R^{s6}$ independently at each occurrence indicates a hydrogen atom or a monovalent hydrocarbon group), —$N(R^{s7})$—(C═O)—$R^{s8}$ (wherein $R^{s7}$ indicates a hydrogen atom or a monovalent hydrocarbon group, and $R^{s2}$ indicates a monovalent hydrocarbon group), —$SO_2$—$R^{s9}$ (wherein $R^{s9}$ indicates hydroxy or a monovalent hydrocarbon group), —S(═O)—$R^{s10}$ (wherein $R^{s10}$ indicates hydroxy or a monovalent hydrocarbon group), nitro, cyano, and halogen atoms.

Here, examples of the halogen atoms include a fluorine atom, a chlorine atom, a bromine atom and an iodine atom, with a fluorine atom and a chlorine atom being preferable.

The substituent is preferably one or more kinds of substituents selected from the group consisting of monovalent hydrocarbon groups (optionally further substituted with a halogen atom), nitro, cyano and halogen atoms.

The electron-withdrawing groups are:

preferably one or more kinds of groups selected from the group consisting of —C(═O)—$OR^1$, —S(═O)$_2$—$R^2$, —P(═O)(—$OR^3$)$_2$, cyano, halogen-substituted alkyls, carboxy, nitro, —S(═O)—$R^4$, —C(═O)—$R^5$ and —C(═O)—$NR^6R^7$;

more preferably one or more kinds of groups selected from the group consisting of —C(═O)—$OR^1$, —S(═O)$_2$—$R^2$, —P(═O)(—$OR^3$)$_2$, cyano, halogen-substituted alkyls and carboxy; and still more preferably one or more kinds of groups selected from the group consisting of —C(═O)—$OR^1$, —S(═O)$_2$—$R^2$, —P(═O)(—$OR^3$)$_2$ and cyano.

Here, $R^1$, $R^2$, $R^3$, $R^4$, $R^5$, $R^6$ and $R^7$ are the same as defined hereinabove.

$R^1$ is preferably a monovalent hydrocarbon group, more preferably a monovalent chain hydrocarbon group, still more preferably an alkyl, and particularly preferably an alkyl having a carbon number of 1 to 4.

$R^2$ is preferably a monovalent hydrocarbon group, more preferably a monovalent aromatic hydrocarbon group, still more preferably an aryl, and particularly preferably phenyl.

$R^3$ is preferably a monovalent hydrocarbon group, more preferably a monovalent chain hydrocarbon group, and still more preferably an alkyl.

$R^4$ is preferably a monovalent hydrocarbon group, more preferably a monovalent aromatic hydrocarbon group, and still more preferably an aryl.

$R^5$ is preferably a monovalent hydrocarbon group, more preferably a monovalent aromatic hydrocarbon group, and still more preferably an aryl.

$R^6$ is preferably a hydrogen atom or a monovalent hydrocarbon group, and more preferably a hydrogen atom.

$R^7$ is preferably a hydrogen atom or a monovalent hydrocarbon group, more preferably a monovalent hydrocarbon group, still more preferably a monovalent chain hydrocarbon group or a monovalent aromatic hydrocarbon group, and particularly preferably an alkyl or an aryl.

From points of view such as enhancing the reactivity with the organic substance, the olefin compound is preferably a compound represented by the following formula (I):

(I)

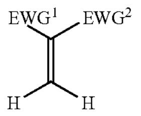

In the formula (I), $EWG^1$ and $EWG^2$ each independently indicate an electron-withdrawing group, and may form a ring together with the carbon atom to which they are bonded.

Preferred examples of the electron-withdrawing groups are the same as described hereinabove.

$EWG^1$ and $EWG^2$ are preferably identical groups. This configuration may prevent the organic substance from being derivatized into a pair of diastereomers by the reaction between the olefin compound and the organic substance.

The olefin compound can be produced by a conventionally known method. Alternatively, commercially available compounds can be used as the olefin compounds.

1.3. Reaction Conditions

In the production method according to the present embodiment, the organic substance and the olefin compound are reacted under an acidic condition. In this manner, the oxidation reaction of the group A contained in the organic substance can be suppressed. Furthermore, when an oxidant such as a disulfide compound is present in the reaction system, the reaction between the group A and the oxidant can be suppressed. As a result, the organic substance can be efficiently converted into a derivative.

The term "acidic condition" means that the reaction of the organic substance and the olefin compound is carried out in an acidic solution. The organic substance and the olefin compound are not necessarily dissolved completely in the acidic solution, and the reaction may be performed in a state in which the organic substance and the olefin compound are dispersed in the acidic solution.

The acidic solution usually has a pH of less than 7, preferably a pH of 6.5 or less, more preferably a pH of 6.0 or less, still more preferably a pH of less than 6.0, and particularly preferably a pH of 5.5 or less, a pH of 5.25 or less, a pH of 5.0 or less, a pH of 4.75 or less, a pH of 4.5 or less, or a pH of 4.25 or less, and preferably has a pH of 0.0 or more, and more preferably a pH of 2.0 or more. By controlling the pH of the acidic solution to the above range, side reactions such as the oxidation of the organic substance and the exchange reaction with a disulfide compound can be effectively suppressed while suppressing the decomposition of the derivative.

Here, the pH of the acidic solution and the pH of a neutral or basic solution described later can be measured at a temperature of 25° C. with a pH meter using a glass electrode method.

The acidic solution is preferably a solution containing water. The acidic solution may contain an organic solvent in addition to water. The organic solvent is preferably a solvent that can be mixed with water in any ratio. Examples of such organic solvents include alcohol solvents such as methanol and ethanol; nitrile solvents such as acetonitrile; and aprotic polar solvents such as dimethyl sulfoxide, dimethylformamide, dioxane and tetrahydrofuran.

When the acidic solution is a solution containing water, the weight percentage of an organic solvent in the solution relative to water is preferably 50 wt % or less, more preferably 10 wt % or less, and still more preferably 5 wt % or less, and is usually 0 wt % or more.

More preferably, the acidic solution is an aqueous solution.

The acidic solution usually includes an acid. Examples of the acids include inorganic acids and organic acids. Examples of the inorganic acids include phosphoric acid, hydrochloric acid, sulfuric acid and perchloric acid. Examples of the organic acids include formic acid, oxalic acid, acetic acid, trifluoroacetic acid, methanesulfonic acid, trifluoromethanesulfonic acid, toluenesulfonic acid and cyanoacetic acid.

The acidic solution may be a buffer solution adjusted to a desired pH.

The reaction temperature under the acidic condition is not particularly limited, but is preferably 50° C. or lower, more preferably 45° C. or lower, and still more preferably 40° C. or lower, and is preferably 5° C. or higher, more preferably 10° C. or higher, and still more preferably 15° C. or higher.

The reaction time under the acidic condition is not particularly limited, but is preferably 60 minutes or less, more preferably 30 minutes or less, and still more preferably 15 minutes or less, and is usually 0 minute or more.

Usually, the reaction under an acidic condition is carried out by mixing the organic substance and the olefin compound together in an acidic solution.

The organic substance and the olefin compound may be mixed together in an acidic solution in any manner without limitation. For example, a method (1) may be adopted in which an acidic solution containing the organic substance is prepared, and the olefin compound is admixed therewith. In another exemplary method (2), a solution containing the organic substance is prepared, a buffer solution or the like is added thereto to adjust the pH to a desired range, and thereafter the olefin compound is admixed therewith.

To suppress the oxidation reaction of the organic substance, it is preferable that an acidic solution containing the organic substance be prepared, and that the olefin compound be admixed with the solution. The olefin compound may be added as such or in the form of a solution in a solvent (water or an organic solvent).

The concentration of the organic substance in the acidic solution is not particularly limited, but may be, for example, 0.1 μmol/L to 100 mmol/L.

The amount of the olefin compound relative to the organic substance is not particularly limited, but may be, for example, 1 to 100 when expressed in molar ratio.

When the organic substance contains an amino group in addition to the group A, the organic substance may be derivatized by the reaction with the olefin compound under an acidic condition and subsequently under an neutral or basic condition (preferably under an basic condition).

In the above case, the group A contained in the organic substance reacts with the olefin compound under an acidic condition and is converted into a stable substituent to side reactions such as oxidation. Under a subsequent neutral or basic condition, the amino group (that may be an unsubstituted amino group, a monosubstituted amino group or a disubstituted amino group) contained in the organic substance reacts with the olefin compound and is converted into a substituted amino group (a substituted ammonio group in the case where the amino group contained in the organic substance is a disubstituted amino group) that has a substituent derived from the olefin compound.

By the production method described above, both the group A contained in the organic substance and an amino group possibly contained in the organic substance react with the olefin compound to give a derivative that has substituents converted from both the group A and the amino group.

A derivative that contains an amino group resulting from substitution to a higher degree has productional and analytical advantages as compared to a derivative that contains the corresponding amino group before the substitution. Usually, an amino group resulting from substitution to a higher degree has enhanced hydrophobicity as compared to the corresponding amino group before the substitution. Thus, it is often the case that separation conditions for a derivative of an organic substance may be determined easily in liquid chromatography. On the other hand, a derivative that contains an amino group with a low degree of substitution (for example, a derivative containing an unsubstituted amino group, such as cysteine or reduced glutathione) is highly hydrophilic, and thus provides weak retention in reversed-phase liquid chromatography and provides very strong retention in hydrophilic interaction liquid chromatography (HILIC), making it difficult to determine separation conditions in some cases. Furthermore, a derivative that contains an amino group resulting from substitution to a higher degree is often detected with high sensitivity with a mass spectrometer as compared to a derivative that contains the corresponding amino group before the substitution.

The term "neutral or basic condition" means that the organic substance reacted under an acidic condition (hereinafter, also written as the acidic condition derivative) is reacted with the olefin compound in a neutral or basic solution. The acidic condition derivative and the olefin compound are not necessarily dissolved completely in the solution, and the reaction may be performed in a state in which the acidic condition derivative and the olefin compound are dispersed in the solution.

The neutral or basic solution usually has a pH of 7 or more, preferably a pH of 7.5 or more, more preferably a pH of 8 or more, and still more preferably a pH of 8.5 or more, and preferably has a pH of 11 or less, more preferably a pH of 10 or less, and still more preferably a pH of 9.5 or less. By controlling the pH of the neutral or basic solution to the above range, the reaction can be promoted between an amino group that may be present in the organic substance and the olefin compound, while suppressing the decomposition of the derivative.

The neutral or basic solution is preferably a solution containing water. The neutral or basic solution may contain an organic solvent in addition to water. The organic solvent is preferably a solvent that can be mixed with water in any ratio. Examples of such organic solvents include those organic solvents mentioned in the description of the acidic solution.

When the neutral or basic solution is a solution containing water, the weight ratio of an organic solvent in the solution relative to water may fall in the preferred range mentioned in the description of the acidic solution. More preferably, the neutral or basic solution is an aqueous solution.

The basic solution usually contains a base. Examples of the bases include inorganic bases and organic bases. Examples of the inorganic bases include metal hydroxides (for example, sodium hydroxide, potassium hydroxide, and calcium hydroxide), metal carbonate salts (for example, sodium carbonate, sodium hydrogen carbonate, and potassium carbonate), sodium phosphate, potassium phosphate, ammonia, sodium borate and potassium borate. Examples of the organic bases include amines (for example, trimethylamine and triethylamine).

The neutral or basic solution may be a buffer solution adjusted to a desired pH.

The reaction temperature under a neutral or basic condition is not particularly limited, but is preferably 50° C. or lower, more preferably 45° C. or lower, and still more preferably 40° C. or lower, and is preferably 5° C. or higher, more preferably 10° C. or higher, and still more preferably 15° C. or higher.

The reaction time under a neutral or basic condition is not particularly limited, but is preferably 60 minutes or less, more preferably 30 minutes or less, and still more preferably 15 minutes or less, and is usually 0 minute or more.

Usually, the reaction under a neutral or basic condition is carried out by mixing the acidic condition derivative and the olefin compound together in a neutral or basic solution.

The acidic condition derivative may be mixed together with the olefin compound in a neutral or basic solution after the acidic condition derivative is isolated from the acidic solution. Alternatively, the acidic solution containing the acidic condition derivative may be adjusted to a desired neutral or basic pH without the isolation of the acidic condition derivative, and the acidic condition derivative may be mixed together with the olefin compound in the neutral or basic solution.

When the acidic condition derivative is, without isolation, mixed together with the olefin compound in the solution as described above, the olefin compound may be newly added to the solution. Alternatively, an excess amount of the olefin compound may be added beforehand in the reaction under an acidic condition, and the excess olefin compound may be used in the reaction under a neutral or basic condition.

For example, the formation of a derivative of the organic substance can be confirmed by a method such as liquid chromatography or mass spectrometry.

The derivative production method of the present embodiment may include optional steps in addition to the reaction step in which the organic substance is reacted with the olefin compound. Examples of such optional steps include a step in which the reaction solution containing the derivative is diluted after the reaction step, and a step in which the derivative is isolated from the reaction solution.

In the derivative of the organic substance produced by the above method, the group A has been converted into a group that is more stable to oxidation. Thus, the derivative of the organic substance can be analyzed more accurately than when the organic substance is analyzed directly.

2. Methods for Analyzing Samples Containing Organic Substances

A method for analyzing a sample containing an organic substance according to an embodiment of the present invention includes: (1) mixing a sample that contains an organic substance containing one or more kinds of groups selected from the group consisting of sulfanyl, selanyl and sulfino, and an olefin compound that contains an ethylene structure having at least two electron-withdrawing groups except halogen atoms under an acidic condition to form a treated sample containing a derivative of the organic substance; and (2) analyzing the derivative of the organic substance in the treated sample.

2.1. Step (1)

At Step (1), a sample that contains an organic substance containing one or more kinds of groups (groups A) selected from the group consisting of sulfanyl, selanyl and sulfino, and an olefin compound that contains an ethylene structure having at least two electron-withdrawing groups except halogen atoms are mixed together under an acidic condition to form a treated sample containing a derivative of the organic substance.

Examples and preferred examples of the organic substances include those described hereinabove. The sample may contain a plurality of kinds of organic substances.

Examples of the samples containing an organic substance include, but are not particularly limited to, biological samples derived from living organisms, and nonbiological samples such as synthetic samples obtained by organic synthesis reactions, and environmental samples present in the natural environment. Examples of the living organisms from which biological samples are derived include animals such as mammals (for example, humans, monkeys, mice, rats, rabbits, cows, pigs, horses, goats, and sheep) and birds, insects, mollusks, microorganisms and plants, with mammals being preferable. Exemplary types of biological samples include blood samples (for example, whole blood, serum, and plasma), saliva, urine, feces, bile, sweat, tears, cerebrospinal fluids, culture media after use for culturing of cells or microorganisms, and tissue and cell extracts. Examples of the synthetic samples include reaction products obtained by organic synthesis reactions that produce organic substances, and media used for culturing of cells or microorganisms. Examples of the environmental samples include samples from soil, seawater and freshwater.

The concentrations of the organic substance and the olefin compound in the sample are not particularly limited as long as they react to form a derivative of the organic substance and the product can be analyzed. For example, the concentrations of the organic substance and the olefin compound in the sample may be each, for example 0.001 μmol/L to 1,000 mmol/L, preferably 0.01 μmol/L to 100 mmol/L, more preferably 0.1 μmol/L to 10 mmol/L, and still more preferably 1 μmol/L to 1 mmol/L.

The sample may be a sample that has been pretreated, for example, deproteinized.

In the analysis method of the present embodiment, the sample is treated under an acidic condition. This fact is advantageous in that the sample that has been subjected to acidic pretreatment, for example, deproteinization treatment can be mixed together with the olefin compound while keeping the sample acidity acidic, that is, without adjusting the acidity of the sample to neutral or basic. An acidic condition inhibits the progress of side reactions such as the oxidation reaction of the group A, and the exchange reaction between the group A and disulfide. Thus, the progress of side reactions between the pretreatment and the analysis can be retarded. As a result, the organic substance having the group A can be analyzed more accurately.

The sample may contain a disulfide compound. A disulfide compound is a compound that contains a group represented by —S—S—. A disulfide compound can be generated by the oxidation of a thiol.

For example, the quantitative ratio of a thiol (for example, cysteine, and reduced glutathione) to a disulfide compound (for example, cystine, and oxidized glutathione) in a biological sample is useful information for knowing the redox state of the biological sample.

In the analysis method of the present embodiment, the organic substance that contains an oxidation-labile group A such as sulfanyl is analyzed after the organic substance is converted into a derivative by the reaction of the group A with the olefin compound. Furthermore, in the analysis method of the present embodiment, the sample is treated under an acidic condition. As described above, an acidic condition inhibits the progress of the exchange reaction between a thiol and a disulfide compound. Thus, the amount of the organic substance contained in the sample can be accurately determined.

Examples of the disulfide compounds that may be present in the samples include compounds resulting from the intermolecular reaction of sulfanyl that may be contained in the organic substance into disulfide. More specific examples include dimethyl disulfide, diethyl disulfide, oxidized glutathione and cystine.

The disulfide compound that may be present in the sample may contain an amino group. Here, the amino group that may be contained in the disulfide compound may be an unsubstituted amino group (—$NH_2$), a monosubstituted amino group or a disubstituted amino group. The amino group that may be contained in the disulfide compound is preferably one or more selected from the group consisting of unsubstituted amino group and monosubstituted amino groups, and is more preferably an unsubstituted amino group. The disulfide compound may contain only one amino group in the molecule, or may contain a plurality of amino groups in the molecule. The number of amino groups that may be contained in the molecule of the disulfide compound may be 1, 2, 3 or 4, preferably 1, 2 or 3, and more preferably 1 or 2.

In an embodiment, the sample contains one or more selected from the group consisting of oxidized glutathione and cystine.

Examples and preferred examples of the olefin compounds include those described hereinabove.

The sample containing the organic substance, and the olefin compound are mixed together under an acidic condition to give a treated sample containing a derivative of the organic substance.

Preferably, the sample containing the organic substance, and the olefin compound are mixed together in an acidic solution. The type of the acidic solution and the pH of the acidic solution may be similar to the preferred examples described in <1.3. Reaction conditions>.

The mixing method is not particularly limited, and includes a method (1) in which the sample containing the organic substance is mixed together with an acidic solution having a desired pH to give a solution, and the olefin compound is admixed therewith, and a method (2) in which the sample containing the organic substance is diluted with dilute hydrochloric acid, a solvent or the like to give a solution, which is then adjusted to a desired pH by the addition of a buffer solution or the like, and thereafter the olefin compound is admixed therewith.

The treatment temperature and the treatment time are not particularly limited, but may be similar to the preferred examples of the reaction temperature and the reaction time described in <1.3. Reaction conditions>.

When the organic substance further contains an amino group in addition to the group A, Step (1) preferably includes Step (1').

At Step (1'), the sample and the olefin compound are mixed together under an acidic condition and are further mixed under a neutral or basic condition to give a treated sample containing a derivative of the organic substance.

As described hereinabove, the group A contained in the organic substance in the sample reacts with the olefin compound under an acidic condition and is converted into a substituent that is stable to side reactions such as oxidation. Under a subsequent neutral or basic condition, the amino group (that may be an unsubstituted amino group, a mono-substituted amino group or a disubstituted amino group) contained in the organic substance reacts with the olefin compound and is converted into a substituted amino group (a substituted ammonio group in the case where the amino group contained in the organic substance is a disubstituted amino group). The organic substance is thus derivatized. As described hereinabove, an amino group attains enhanced hydrophobicity by being substituted to a higher degree. Thus, liquid chromatography separation conditions can be usually determined easily and the separation can be facilitated when an amino group in a derivative is substituted to a higher degree. Furthermore, an amino-containing derivative may be usually detected with higher sensitivity with a mass spectrometer by converting an amino group with a low degree of substitution to an amino group with a higher degree of substitution.

In some cases, the sample may contain a compound containing an amino group with a low degree of substitution (for example, a disulfide compound containing an unsubstituted amino group). Such a compound is highly hydrophilic, and thus provides weak retention in reversed-phase liquid chromatography and provides very strong retention in hydrophilic interaction liquid chromatography (HILIC), making it difficult to determine separation conditions in some cases.

Even in the above case where the sample contains a compound containing an amino group with a low degree of substitution, such a compound containing an amino group with a low degree of substitution, for example, a disulfide compound containing an unsubstituted amino group reacts with the olefin compound under a neutral or basic condition and the amino group is converted to an amino group with a higher degree of substitution (a substituted ammonio group in the case where the amino group is a disubstituted amino group). Similarly to the derivative of the organic substance, an amino-containing disulfide compound or the like having an increased degree of substitution of the amino group usually allows for easy setting of liquid chromatography separation conditions, and is easily separated, and further may be usually detected with higher sensitivity with a mass spectrometer.

As an example, the analysis method will be described with respect to a case where the organic substance that may be contained in the sample is cysteine and the disulfide compound that may be contained in the sample is cystine formed of two cysteine molecules. It is presumed that when such a sample is mixed together with the olefin compound under an acidic condition, the resultant treated sample that has been obtained under an acidic condition contains cystine and a derivative of cysteine (a first derivative) resulting from the reaction of the sulfanyl group of cysteine with the olefin compound.

The derivative of cysteine has one unsubstituted amino group, and cystine has two unsubstituted amino groups. Due to this, a large difference in hydrophobicity is produced between the derivative of cysteine and cystine. Thus, difficulties are sometimes encountered in determining conditions for simultaneously analyzing the derivative of cysteine and cystine by liquid chromatography.

When the sample and the olefin compound are mixed together under an acidic condition and are further mixed under a neutral or basic condition, it is presumed that the resultant treated sample obtained under a neutral or basic condition contains a derivative of cysteine (a second derivative) resulting from the reaction of the sulfanyl group and the amino group with the olefin compound, and a derivative of cystine resulting from the reaction of the amino groups with the olefin compound.

Because each of the amino groups in cysteine and in cystine reacts with the olefin compound, the derivative of cysteine (the second derivative) and the derivative of cystine have a small difference in hydrophobicity to allow relatively easy setting of liquid chromatography conditions for simultaneously analyzing the derivative of cysteine and the derivative of cystine.

As described above, Step (1) that includes Step (1') enables easy and accurate analysis of the organic substance in the sample that contains an amino group in addition to the group A.

At Step (1'), preferably, the sample containing the organic substance, and the olefin compound are mixed together in an acidic solution and are further mixed in a neutral or basic solution. The type of the neutral or basic solution and the pH of the neutral or basic solution may be similar to the preferred examples described in <1.3. Reaction conditions>.

The method of mixing in the neutral or basic solution is not particularly limited, and includes a method in which the sample and the olefin compound are mixed together in an acidic solution, the resultant mixture solution (the treated sample obtained under an acidic condition) is adjusted to a desired neutral or basic pH by the addition of a basic solution, and the sample and the olefin compound are further mixed in the neutral or basic solution, and a method in which the mixture solution described above may be added to a neutral or basic solution provided separately, and the resultant mixture may be mixed.

The treatment temperature and the treatment time under a neutral or basic condition are not particularly limited, but may be similar to the preferred examples of the reaction temperature and the reaction time under a neutral or basic condition described in <1.3. Reaction conditions>.

By mixing the sample containing the organic substance together with the olefin compound in an acidic solution and further performing mixing in a neutral or basic solution, a treated sample that contains a derivative of the organic substance can be obtained.

2.2. Step (2)

At Step (2), the derivative of the organic substance in the treated sample is analyzed.

Step (2) may include Step (2a) and Step (2b) in this order.

2.2.1. Step (2a)

At Step (2a), the derivative of the organic substance is separated from the treated sample of Step (1).

The separation may be performed by any method capable of separating the derivative from substances other than the derivative (for example, a disulfide compound) contained in the treated sample.

Examples of the separation methods include, but are not particularly limited to, liquid chromatography, supercritical fluid chromatography (SFC), capillary electrophoresis (CE) and gas chromatography (GC). The separation method may be selected appropriately in accordance with the types and properties of contaminants contained in the sample, and the type and properties of the derivative of the organic substance. A preferred separation method is liquid chromatography, with high-performance liquid chromatography (HPLC) being more preferable. These separation methods may be carried out in a conventionally known manner. The separation methods may be used singly or may be combined.

Examples of the liquid chromatography include reversed-phase liquid chromatography, normal-phase liquid chromatography, hydrophilic interaction liquid chromatography (HILIC), ion-exchange chromatography and size-exclusion chromatography.

Examples of the stationary phases in reversed-phase liquid chromatography include, but are not particularly limited to, silica gels modified with a hydrophobic compound such as octadecylsilane. Examples of the mobile phases include, but are not particularly limited to, organic solvents, aqueous solutions and mixtures thereof. Preferred examples of the organic solvents include acetonitrile, methanol, ethanol and isopropanol (2-propanol). Preferred examples of the aqueous solutions include water, an aqueous formic acid solution, an aqueous ammonium formate solution, an aqueous trifluoroacetic acid solution, an aqueous acetic acid solution, an aqueous ammonium acetate solution, an aqueous ammonium bicarbonate solution and buffer solutions.

Examples of the stationary phases in normal-phase liquid chromatography include, but are not particularly limited to, silica gel and alumina. Examples of the mobile phases include, but are not particularly limited to, hexane, ethyl acetate, methylene chloride, isopropanol, ethanol, methanol, tetrahydrofuran and mixtures thereof.

Examples of the stationary phases in hydrophilic interaction chromatography include, but are not particularly limited to, silica gel and silica gels modified with aminopropyl, amide, diol or cyano. Examples of the mobile phases include, but are not particularly limited to, organic solvents, aqueous solutions and mixtures thereof. Preferred examples of the organic solvents include acetonitrile, methanol, ethanol and isopropanol. Preferred examples of the aqueous solutions include water, an aqueous formic acid solution, an aqueous ammonium formate solution, an aqueous trifluoroacetic acid solution, an aqueous acetic acid solution, an aqueous ammonium acetate solution, an aqueous ammonium bicarbonate solution and buffer solutions.

Hydrophilic interaction chromatography is favorably used when the target of separation is highly hydrophilic and provides weak retention on a stationary phase in reversed-phase chromatography. For example, hydrophilic interaction chromatography can simultaneously analyze a disulfide compound such as cystine or oxidized glutathione that is not derivatized by the olefin compound, and a thiol derivative such as a cysteine derivative or a reduced glutathione derivative.

When the organic substance is a mixture of chiral compounds, the chiral compounds may be separated by any liquid chromatography using a column filled with a chiral filler (a chiral column).

For example, a derivative of D-cysteine (having a low abundance ratio in nature) and a derivative of L-cysteine can be separated with a chiral column.

2.2.2. Step (2b)

At Step (2b), the separated derivative of the organic substance is detected.

Examples of the detection methods include, but are not particularly limited to, mass spectrometry using a mass spectrometer, ultraviolet absorption detection (UV), photodiode array detection (PDA), fluorescence detection (FL), visible light absorption detection, inductively coupled plasma emission spectroscopy (ICP), corona charged aerosol detection, differential refractive index detection (RI) and evaporation light scattering detection (ELSD). The detection method may be selected appropriately in accordance with the types and properties of contaminants contained in the sample, and the type and properties of the derivative of the organic substance.

Preferred detection methods are mass spectrometry, ultraviolet absorption detection, fluorescence detection, visible light absorption detection and inductively coupled plasma emission spectroscopy, with mass spectrometry and ultraviolet absorption detection being more preferable. These detection methods may be used singly or may be combined.

The detection methods may be carried out in a conventionally known manner.

The mass spectrometry is not particularly limited and may be performed using an appropriate combination of ionization methods, ion separation methods and detectors.

Specific examples of the mass spectrometers used in the mass spectrometry include triple quadrupole mass spectrometers, time-of-flight mass spectrometers (TOF-MS) and ion trap mass spectrometers (for example, Orbitrap (registered trademark) mass spectrometer).

2.3. Optional Steps

The analysis method according to the present embodiment may include optional steps in addition to Steps (1) and (2).

When, for example, the sample that is used contains amino acids, an optional step may be added in which the amino acids are derivatized with an amino acid derivatizing reagent such as ninhydrin or o-phthalaldehyde. The amino acid derivatizing step is preferably performed after Step (1) and before Step (2).

For example, the inclusion of such an optional step offers the following advantage.

For example, it is usually difficult to analyze cysteine and cystine simultaneously with an amino acid analyzer because cysteine and cystine are usually similar in retention time without derivatization. However, Step (1) converts only cysteine into a derivative by the reaction of cysteine and the olefin compound, without cystine being derivatized. As a result, the cysteine after being derivatized with an amino acid derivatizing agent usually has a different retention time from cystine. Thus, cysteine and cystine may be analyzed simultaneously with an amino acid analyzer by the analysis method according to the present embodiment.

3. Derivatizing Agents for Derivatizing Organic Substances Under an Acidic Condition An agent according to an embodiment of the present invention is a derivatizing agent for derivatizing an organic substance containing one or more kinds of groups selected from the group consisting of sulfanyl, selanyl and sulfino under an acidic condition. The derivatizing agent includes an olefin compound including an ethylene structure having at least two electron-withdrawing groups except halogen atoms.

Examples and preferred examples of the olefin compounds include those described hereinabove. Examples and preferred examples of the organic substances include those described hereinabove. The derivatizing agent is used for the production of a derivative under acidic conditions. Preferably, the organic substance is derivatized in an acidic solution containing the derivatizing agent. The type of the acidic solution and the pH of the acidic solution may be similar to the preferred examples described in <1.3. Reaction conditions>.

The concentration of the olefin compound in the derivatizing agent depends on the dilution ratio of the derivatizing agent, and may be, for example, 0.001 μmol/L to 1,000 mol/L, preferably 0.01 μmol/L to 100 mol/L, more preferably 0.1 μmol/L to 10 mol/L, and still more preferably 1 μmol/L to 1 mol/L.

4. Analyzing Reagents for Analyzing Organic Substances

A reagent according to an embodiment of the present invention is an analyzing reagent for analyzing an organic substance containing one or more kinds of groups selected from the group consisting of sulfanyl, selanyl and sulfino. The analyzing reagent includes the derivatizing agent described above.

Examples and preferred examples of the olefin compounds include those described hereinabove. Examples and preferred examples of the organic substances include those described hereinabove.

The concentration of the olefin compound in the analyzing reagent depends on the dilution ratio of the analyzing reagent, and may be, for example, 0.001 μm/L to 1,000 mol/L, preferably 0.01 μmol/L to 100 mol/L, more preferably 0.1 μmol/L to 10 mol/L, and still more preferably 1 μmol/L to 1 mol/L.

The analyzing reagent is preferably used in the sample analysis method described hereinabove that includes Steps (1) and (2).

Other features of the invention will become apparent in the course of the following descriptions of exemplary embodiments which are given for illustration of the invention and are not intended to be limiting thereof.

EXAMPLES

The operations described below were performed at room temperature under atmospheric pressure unless otherwise specified.

Description of Abbreviations

In the following, materials are abbreviated as follows.

Olefin Compounds (Derivatizing Agents)

EMM: Diethyl methylenemalonate

BPSE: 1,1-Bis(phenylsulfonyl)ethylene

BEPE: 1,1-Bis(diethoxyphosphoryl)ethylene

NEM: N-Ethylmaleimide

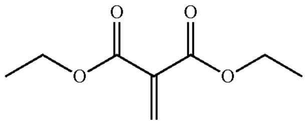

EMM

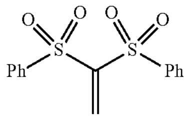

BPSE

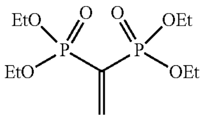

BEPE

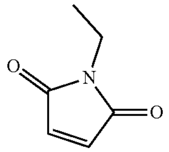

NEM

In the above chemical formulas, "Ph" denotes phenyl and "Et" denotes ethyl.

Organic Substances (Chalcogen-Containing Compounds)

Thiols

Cys: Cysteine

Cys2: Cystine

GSH: Reduced glutathione

GSSG: Oxidized glutathione gEC: γ-Glutamylcysteine

CG: Cysteinylglycine

Hcy: Homocysteine

NAC: N-Acetylcysteine

Cysteine Persulfides

Cys-SH: S-mercaptocysteine

Cys-SSH: S-disulfanylcysteine

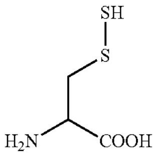

(Cys-SH)

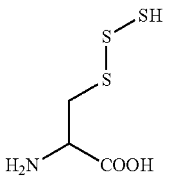

(Cys-SSH)

Device and Analysis Method

LC-MS/MS: Liquid chromatograph-tandem mass spectrometer

HILIC: Hydrophilic interaction liquid chromatography (hydrophilic interaction chromatography)

Examples A: Examples Using EMM and NEM

Example A1 Reactions of EMM and NEM with Cysteine (Cys) Under Acidic Conditions In this Example, the reactivities of EMM and NEM under acidic conditions were estimated from the amount of residual Cys after the reaction. Furthermore, a peak assigned to EMM-derivatized Cys was identified by LC-MS/MS.

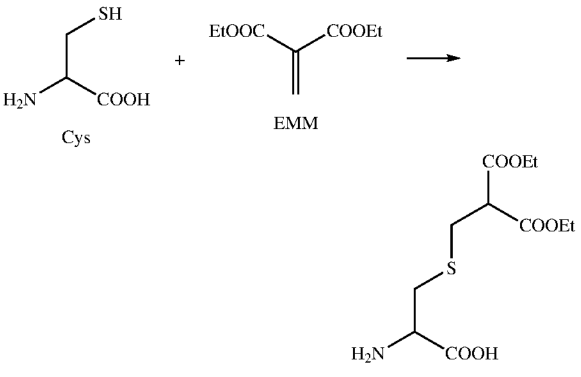

Cys EMM

EMM-Cys

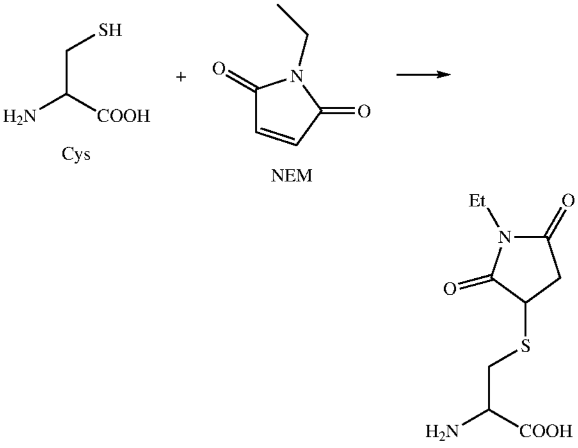

Cys NEM

NEM-Cys

A1-1. Production of Derivatives

L-Cysteine hydrochloride (manufactured by Sigma) was dissolved into a 0.1% formic acid solution (manufactured by FUJIFILM Wako Pure Chemical Corporation, diluted with pure water) so that the concentration would be 10 mmol/L. The derivatizing agent EMM (manufactured by Asta Tech) was dissolved into acetonitrile (manufactured by FUJIFILM Wako Pure Chemical Corporation) so that the concentration would be 10 μL/mL. The derivatizing agent NEM (manufactured by Wako Pure Chemical Industries, Ltd.) was dissolved into acetonitrile so that the concentration would be 10 mg/mL. To 10 μL of the cysteine solution, 10 μL of the derivatizing agent solution (EMM or NEM) or 10 μL of acetonitrile was added. The mixtures were allowed to stand at room temperature for 10 minutes. After the reaction, 980 μL of 0.1% formic acid was added, and the mixtures were stirred sufficiently. Sample solutions were thus prepared.

A1-2. Analysis of Derivatives

The sample solutions were analyzed by LC-MS/MS under the following conditions. LC that was used was Agilent 1200 series (manufactured by Agilent), and the tandem mass spectrometer that was used was 3200 QTRAP system (manufactured by Sciex).

LC Conditions

Mobile phase solution A: 0.1% formic acid, mobile phase solution B: acetonitrile Gradient conditions: 5-80% B (0-8 min), 80% B (8-10 min), 80-5% B (10-10.5 min), and 5% B (10.5-15 min)

Column: XBridge C18 3.5 μm, 2.1×100 mm (manufactured by Waters)

Column temperature: 40° C.

Flow rate: 0.4 mL/min

Injection volume: 1 μL

MS/MS Conditions

The analysis was performed under conditions described in the table below. In the table, "NEM-Cys" and "EMM-Cys" denote Cys derivatized with NEM, and Cys derivatized with EMM, respectively.

TABLE 1

| Compound | Q1 (Da) | Q3 (Da) | Time (ms) | DP (V) | EP (V) | CEP (V) | CE (V) | CXP (V) |
|---|---|---|---|---|---|---|---|---|
| Un-derivatized Cys | 122.000 | 76.0 | 25 | 26 | 7.5 | 8 | 17 | 2 |
| NEM-Cys | 247.153 | 59.0 | 25 | 26 | 6.5 | 12 | 57 | 2 |
| EMM-Cys | 294.205 | 173.3 | 25 | 21 | 9.5 | 32 | 15 | 4 |

Results of Analysis

A peak of underivatized Cys was observed at 1.36 min. Peaks of NEM-Cys were observed at 2.00 min and 2.14 min (since diastereomers are generated, two peaks are observed). A peak of EMM-Cys was observed at 8.23 min. The peaks were each integrated. The measurement was performed twice, and the results of the two measurements were averaged.

The derivatization ratio was calculated by the following equation (1).

$$\text{Derivatization ratio}(\%) = \frac{\text{Underivatized Cyc peak area}(A) - \text{Residual Cyc peak area}(B)\text{ after derivatization}}{\text{Underivatized Cyc peak area}(A)} \quad (1)$$

The analysis results are listed in the table below. Exemplary chromatograms are illustrated in FIGS. 1 to 3.

FIG. 1 is an exemplary chromatogram illustrating a peak of cysteine.

Figure 2:
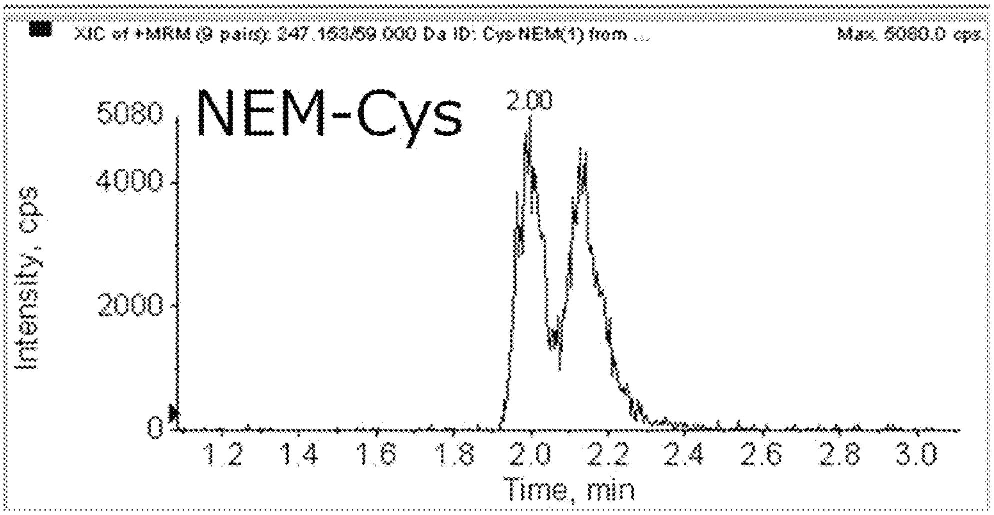
FIG. 2 is an exemplary chromatogram illustrating a peak of NEM-Cys.

FIG. 2 is an exemplary chromatogram illustrating peaks of NEM-Cys.

Figure 3:
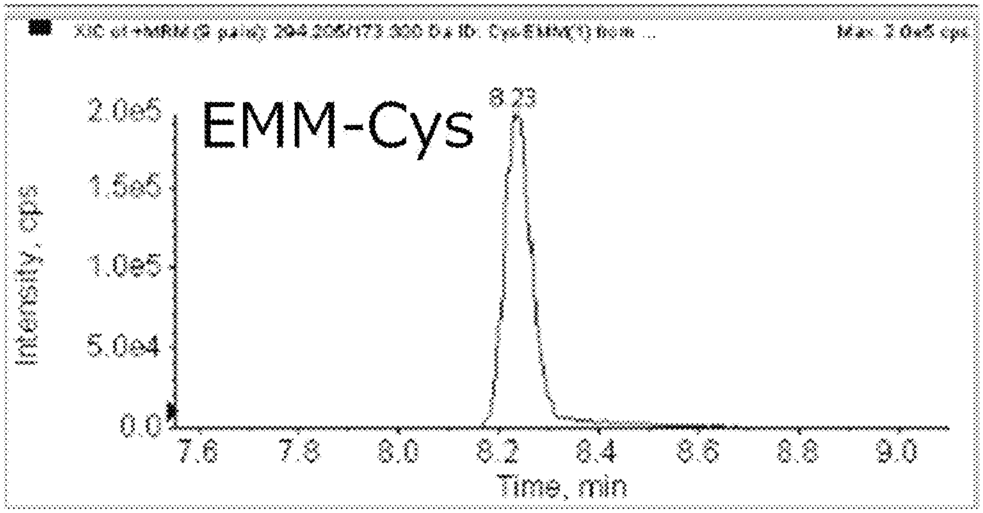
FIG. 3 is an exemplary chromatogram illustrating a peak of EMM-Cys.

FIG. 3 is an exemplary chromatogram illustrating a peak of EMM-Cys.

TABLE 2

| | Cys peak area (count) | Derivatization ratio (%) | Derivatized Cys peak area (count) |
|---|---|---|---|
| Underivatized Cys | 6.21E+04 (A) | — | — |
| NEM-Cys | 2.51E+04 (B) | 60 | 4.81E+04 |
| EMM-Cys | 1.62E+03 (B) | 97 | 4.12E+05 |

The results indicate that NEM and EMM are each capable of derivatizing Cys with a high reaction ratio under acidic conditions and mild temperature conditions (room temperature). In particular, EMM achieved a higher reaction ratio than NEM. The derivatization of Cys as a chiral compound with NEM resulted in diastereomers, and the NEM-Cys peak was split into two. On the other hand, the derivatization of Cys with EMM did not produce diastereomers and the peak was not split.

Example A2 Simultaneous Detection and Quantification (Separation by Reversed-Phase LC) of EMM-Derivatized Thiols In this Example, six types of thiol compounds derivatized with EMM under acidic conditions were simultaneously separated and detected using LC-MS/MS.

A2-1. Production of Derivatives

A 0.01 mol/L hydrochloric acid standard thiol mixture solution (a product manufactured by FUJIFILM Wako Pure Chemical Corporation was diluted with pure water) was prepared that contained each 25 μmol/L of L-cysteine hydrochloride, reduced glutathione (GSH) (manufactured by FUJIFILM Wako Pure Chemical Corporation), D,L-homocysteine (Hcy) (manufactured by Sigma), cysteinylglycine (CG) (manufactured by Bachem), γ-glutamylcysteine (gEC) (manufactured by Sigma) and N-acetylcysteine (NAC) (manufactured by JUNSEI CHEMICAL CO., LTD.). To 60 μL of a 20 mmol/L sodium phosphate buffer solution (pH 2.5) (a product manufactured by NACALAI TESQUE, INC. was diluted with pure water), 10 μL of the standard thiol solution was added, 10 μL of an EMM acetonitrile solution (10 μL/mL) was added, and the mixture was stirred and was allowed to stand at room temperature for 10 minutes. Then, 220 μL of a 0.1% formic acid solution was added, and the mixture was stirred sufficiently. A sample solution was thus prepared.

A2-2. Analysis of Derivatives

The sample solution was analyzed by LC-MS/MS. LC that was used was Nexera (manufactured by Shimadzu Corporation), and the tandem mass spectrometer that was used was Triple Quad 6500 system (manufactured by Sciex).

LC Conditions

Mobile phase solution A: 0.1% formic acid, mobile phase solution B: acetonitrile Gradient conditions: 15-20% B (0-2.5 min), 20-90% B (2.5-4.0 min), 90% B (4.0-6.0 min), 90-15% B (6.0-6.2 min), and 15% B (6.2-8.0 min)

Column: L-Column ODS, 3 μm, 2.1×50 mm (manufactured by Chemicals Evaluation and Research Institute, Japan) fitted with Inertsil ODS-3, 3 μm, 1.5×10 mm Guard column for UHPLC (manufactured by GL-Science) as a guard column Column temperature: 40° C.

Flow rate: 0.4 mL/min

Injection volume: 1 μL

MS/MS Conditions

The analysis was performed under conditions listed in the table below.

TABLE 3

| Compound | Q1 (Da) | Q3 (Da) | Time (ms) | DP (V) | EP (V) | CE (V) | CXP (V) |
|---|---|---|---|---|---|---|---|
| Cys | 294.2 | 173.2 | 10 | 46 | 10 | 15 | 4 |
| GSH | 480.2 | 173.2 | 10 | 91 | 10 | 31 | 10 |
| Hcy | 308.2 | 173.2 | 10 | 96 | 10 | 17 | 10 |
| CG | 351.2 | 173.2 | 10 | 111 | 10 | 21 | 10 |
| gEC | 423.3 | 173.2 | 10 | 6 | 10 | 17 | 10 |
| NAC | 336.2 | 173.2 | 10 | 51 | 10 | 13 | 10 |

Results of Analysis

The analysis results are listed in the table below.

TABLE 4

| Compound | Retention time (min) | Peak area (count) |
|---|---|---|
| Cys | 1.26 | 6.82E+6 |
| GSH | 1.80 | 3.28E+6 |
| Hcy | 1.70 | 5.71E+6 |
| CG | 1.00 | 3.15E+6 |
| gEC | 1.93 | 1.18E+6 |
| NAC | 3.67 | 2.36E+6 |

The results indicate that various types of thiols can be derivatized with EMM in such a manner that the derivatized thiols can be simultaneously separated by reversed-phase LC and detected by MS/MS.

Example A3 Analysis of Sulfinic Acid

In this Example, it has been demonstrated that not only thiol (—SH), but also sulfinic acid (—$SO_2H$) is nucleophilic and is analyzable as an EMM-derivatized form.

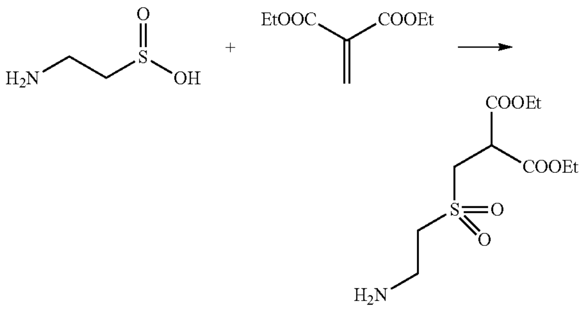

A3-1. Production of Derivative

Hypotaurine (manufactured by Sigma) was dissolved into 0.01 mol/L hydrochloric acid so that the concentration would be 1 mmol/L. To 60 μL of a 20 mmol/L sodium phosphate buffer solution (pH 2.5), 10 μL of the above standard hypotaurine solution was added, and 10 μL of an EMM acetonitrile solution (10 μL/mL) was added. The mixture was stirred and was allowed to stand at room temperature for 10 minutes. Then, 920 μL of a 0.1% formic acid solution was added. The mixture was stirred sufficiently to give a sample solution.

A3-2. Analysis of Derivative

The sample solution was analyzed by LC-MS/MS under the following conditions. LC that was used was Agilent 1200 series (manufactured by Agilent), and the tandem mass spectrometer that was used was 3200 QTRAP system (manufactured by Sciex).

Mobile phase solution A: 0.1% formic acid, mobile phase solution B: acetonitrile Gradient conditions: 15-40% B (0-3.0 min), 40-90% B (3.0-3.2 min), 90% B (3.2-5.5 min), 90-15% B (5.5-5.8 min), and 15% B (5.8-9.5 min)

Column: L-Column ODS, 3 μm, 2.1×50 mm (manufactured by Chemicals Evaluation and Research Institute, Japan) fitted with Inertsil ODS-3, 3 μm, 1.5×10 mm Guard column for UHPLC (manufactured by GL-Science) as a guard column Column temperature: 40° C.

Flow rate: 0.4 mL/min

Injection volume: 10 μL

MS/MS Conditions

The analysis was performed under conditions listed in the table below.

TABLE 5

| Compound | Q1 (Da) | Q3 (Da) | Time (ms) | DP (V) | EP (V) | CEP (V) | CE (V) | CXP (V) |
|---|---|---|---|---|---|---|---|---|
| Hypotaurine | 282.1 | 110.0 | 20 | 16 | 9 | 14 | 13 | 4 |

Results of Analysis

The analysis results are listed in the table below. An exemplary chromatogram is illustrated in FIG. 4.

Figure 4:
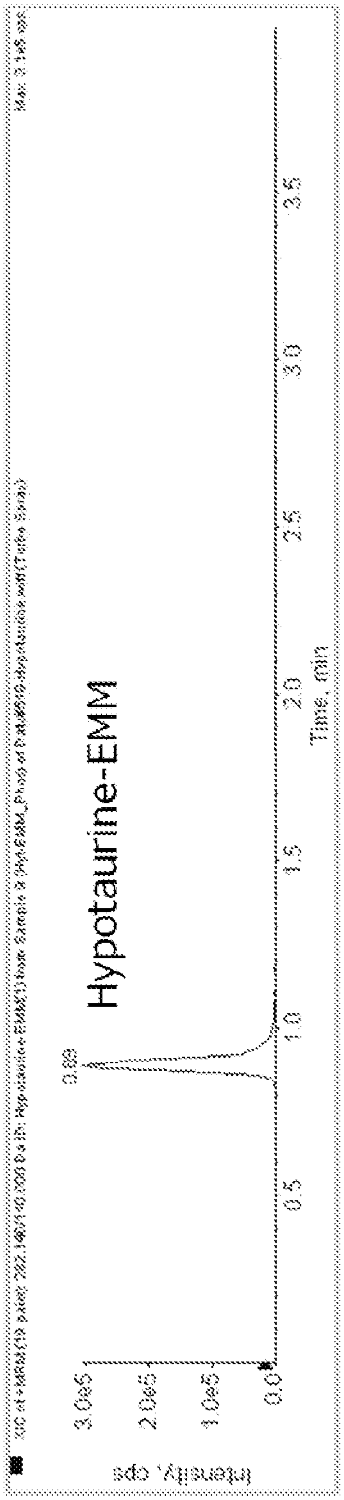
FIG. 4 is an exemplary chromatogram illustrating a peak of EMM-derivatized hypotaurine.

FIG. 4 is an exemplary chromatogram illustrating a peak of EMM-derivatized hypotaurine.

TABLE 6

| Compound | Retention time (min) | Peak area (count) |
|---|---|---|
| Hypotaurine | 0.89 | 8.44E+5 |

The results indicate that a sulfinic acid such as hypotaurine can be derivatized with EMM under acidic conditions and can be analyzed.

Example A4 Analysis of Persulfides

In this Example, it has been demonstrated that persulfides can be derivatized and analyzed. Cysteine persulfides (Cys-SH and Cys-SSH) were used as the persulfides.

Cysteine persulfides have important functions related to redox state in living bodies. Therefore, according to the present invention, the ability to derivatize persulfides while maintaining their redox state offers usefulness in grasping the redox state in a living body.

A4-1. Production of Derivatives

Together with 70 μL of an ammonium formate solution having a pH of 6.7 (manufactured by FUJIFILM Wako Pure Chemical Corporation), 10 μL of a 100 mmol/L L-cysteine solution, 10 μL of a 100 mmol/L aqueous sodium sulfide solution (a product manufactured by FUJIFILM Wako Pure Chemical Corporation was diluted with pure water), and 10 μL of a 0.1% aqueous hydrogen peroxide solution (a product manufactured by KANTO CHEMICAL CO., INC. was diluted with pure water) were mixed. The mixture was reacted at 30° C. for 30 minutes to generate cysteine persulfides in the system. To 10 μL of the above solution, 60 μL of a 20 mmol/L sodium phosphate buffer solution (pH 2.5) and 10 μL of an EMM acetonitrile solution (10 μL/mL) were added. The mixture was stirred and was allowed to stand at room temperature for 10 minutes. After 420 μL of a 0.1% formic acid solution was added, the mixture was stirred sufficiently to give a sample solution.

A4-2. Analysis of Derivatives

The sample solution was analyzed by LC-MS/MS under the following conditions. LC that was used was Agilent 1200 series (manufactured by Agilent), and the tandem mass spectrometer that was used was 3200 QTRAP system (manufactured by Sciex).

LC Conditions

Mobile phase solution A: 0.1% formic acid, mobile phase solution B: acetonitrile Gradient conditions: 15-40% B (0-3.0 min), 40-90% B (3.0-3.2 min), 90% B (3.2-5.5 min), 90-15% B (5.5-5.8 min), and 15% B (5.8-9.5 min)

Column: L-Column ODS, 3 μm, 2.1×50 mm (manufactured by Chemicals Evaluation and Research Institute, Japan) fitted with Inertsil ODS-3, 3 μm, 1.5×10 mm Guard column for UHPLC (manufactured by GL-Science) as a guard column Column temperature: 40° C.

Flow rate: 0.4 mL/min

Injection volume: 10 μL

MS/MS Conditions

The analysis was performed under conditions listed in the table below.

TABLE 7

| Compound | Q1 (Da) | Q3 (Da) | Time (ms) | DP (V) | EP (V) | CEP (V) | CE (V) | CXP (V) |
|---|---|---|---|---|---|---|---|---|
| Cys | 294.2 | 173.3 | 20 | 21 | 9.5 | 32 | 32 | 4 |
| Cys-SH | 326.0 | 173.0 | 20 | 41 | 5.5 | 10 | 35 | 4 |
| Cys-SSH | 358.0 | 173.0 | 20 | 41 | 5.5 | 40 | 19 | 4 |

Results of Analysis

The analysis results are listed in the table below. An exemplary chromatogram is illustrated in FIG. 5.

Figure 5:
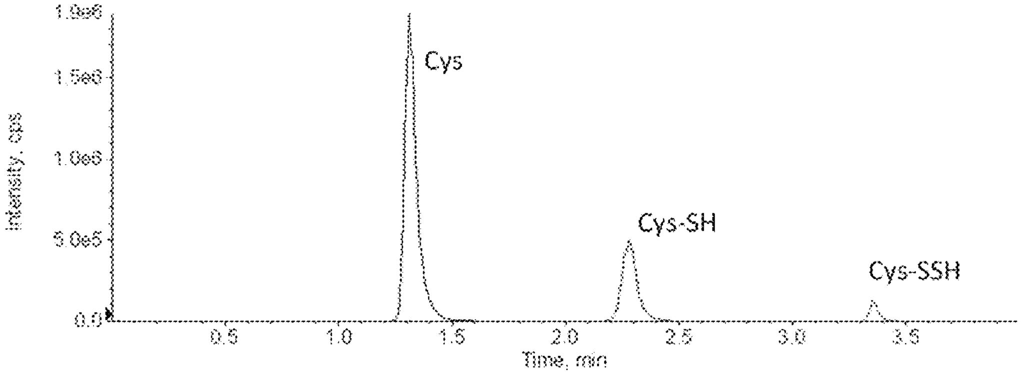
FIG. 5 is an exemplary chromatogram illustrating peaks of EMM-derivatized cysteine and EMM-derivatized cysteine persulfides.

FIG. 5 is an exemplary chromatogram illustrating peaks of EMM-derivatized cysteine and EMM-derivatized cysteine persulfides.

TABLE 8

| | Retention time (min) | Peak area (count) |
|---|---|---|
| Cys | 1.31 | 7.12E+6 |
| Cys-SH | 2.28 | 2.35E+6 |
| Cys-SSH | 3.36 | 3.45E+5 |

The results indicate that persulfides such as cysteine persulfide can be derivatized with EMM under acidic conditions and can be analyzed.

Example A5 Simultaneous Analysis of Cys, Cys2 and Amino Acids Using Amino Acid Analyzer In this Example, it has been demonstrated that Cys, Cys2 and amino acids can be analyzed simultaneously using an amino acid analyzer.

Outline of Analysis Method

A sample was treated with EMM to derivatize Cys and Cys2, and amino acids were separated from the sample using an ion-exchange column. Next, the amino acids were derivatized with ninhydrin by a post-column derivatization method, and Cys, Cys2 and the amino acids were analyzed simultaneously.

In an amino acid analyzer, Cys and Cys2 are usually eluted from the column at the same time and therefore it is usually difficult to analyze Cys and Cys2 simultaneously.

A5-1. Production of Derivatives

To 100 μL of an amino acid mixture standard solution, type H (manufactured by FUJIFILM Wako Pure Chemical Corporation) (a solution containing 2.5 mmol/L of each of L-aspartic acid, L-threonine, L-serine, L-glutamic acid, L-proline, glycine, L-alanine, L-cystine, L-valine, L-methionine, L-isoleucine, L-leucine, L-tyrosine, L-phenylalanine, L-lysine, L-histidine, ammonium chloride and L-arginine), 25 μL of a 10 mmol/L aqueous cysteine hydrochloride solution and 125 μL of pure water were added to give a mixture standard solution. To 100 μL of the standard solution, 200 μL of a 20 mmol/L sodium phosphate buffer solution (pH 2.5) and 50 μL of an EMM acetonitrile solution (5 μL/mL) were added. The mixture was stirred and was allowed to stand at room temperature for 10 minutes. After the reaction, 650 μL of 0.01 mol/L hydrochloric acid was added. A sample solution was thus prepared.

A5-2. Analysis of Derivatives

The sample solution was analyzed with the following analyzer.

Analyzer: High-speed amino acid analyzer L-8900 (manufactured by Hitachi, Ltd.)

Analysis method: Method package "Physiological fluid analysis method", Analysis time "148 minutes" was used.

Results of Analysis

The cysteine derivative was eluted with a retention time of 40.3 minutes, and Cys2 was eluted with a retention time of 48.8 minutes. Other amino acids were eluted with the usual retention times of the analysis method in "Physiological fluid analysis method", Analysis time "148 minutes".

Figure 6:
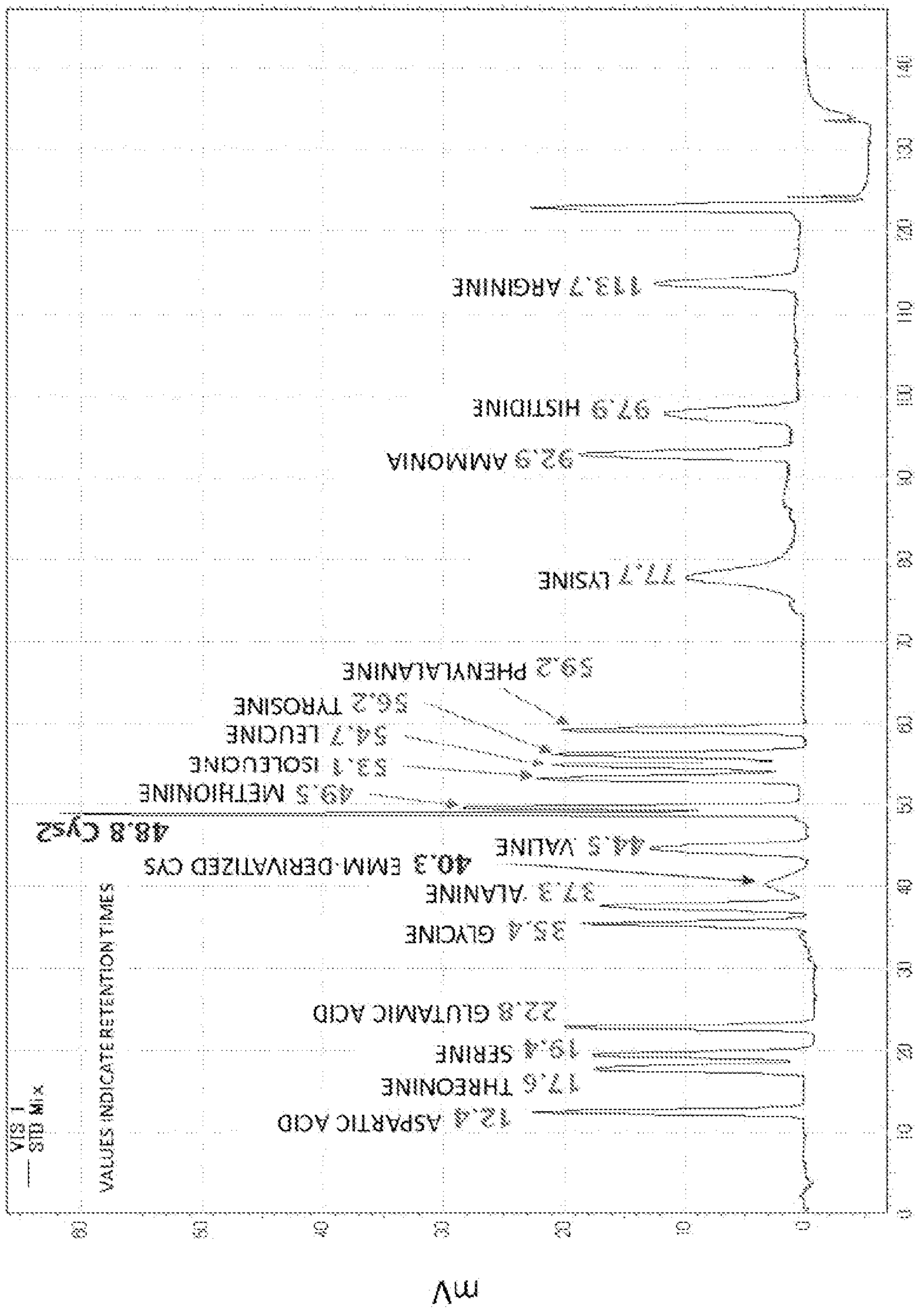
FIG. 6 is an exemplary chromatogram illustrating results of simultaneous analysis of Cys, Cys2 and amino acids using an amino acid analyzer.

An exemplary chromatogram is illustrated in FIG. 6. FIG. 6 is an exemplary chromatogram illustrating results of simultaneous analysis of Cys, Cys2 and amino acids using an amino acid analyzer.

The results indicate that Cys, Cys2 and other amino acids can be analyzed simultaneously by treating a sample containing these Cys, Cys2 and amino acids under acidic conditions and analyzing the treated sample with a normal amino acid analyzer.

Examples B: Examples Using BPSE

Example B1 Derivatization with BPSE and Analysis

In this Example, it has been demonstrated that a thiol can be derivatized with BPSE and can be analyzed.

An exemplary reaction of a thiol with BPSE is illustrated below.

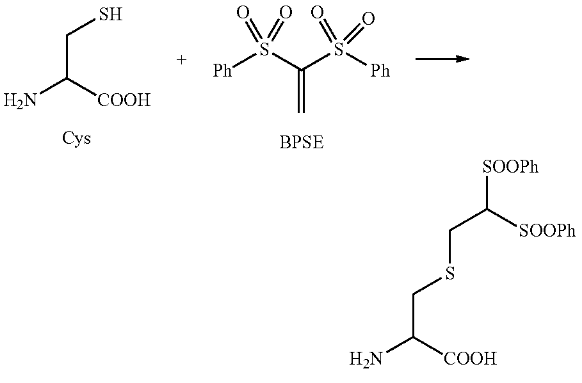

Cys BPSE

BPSE-Cys

B1-1. Production of Derivatives

Six types of 0.01 mol/L hydrochloric acid standard thiol solutions were prepared that contained any of L-Cys, GSH, Hcy, CG, gEC and NAC in a concentration of 10 mmol/L. The standard thiol solutions, each 10 μL, were separately added to 60 μL of a 20 mmol/L sodium phosphate buffer solution (pH 2.5), and 10 μL of a BPSE acetonitrile solution (10 mg/mL) was added. The resultant mixtures were stirred and were allowed to stand at room temperature for 10 minutes. Then, 420 μL of a 0.1% aqueous formic acid solution was added, and the mixtures were stirred sufficiently. Sample solutions were thus prepared.

B1-2. Analysis of Derivatives

The sample solutions were analyzed by LC under the following conditions. Peaks were detected with an HPLC-UV detector.

LC Conditions

Mobile phase solution A: 20 mmol/L sodium phosphate buffer solution (pH 2.5)

Mobile phase solution B: acetonitrile

Gradient conditions: 30% B (0-10 min), 30-90% B (10-11 min), 90% B (11-16 min), 90-30% B (16-16.5 min), and 30% B (16.5-20 min)

Column: Triart C18, 3 μm, 150×4.6 mm (manufactured by YMC)

Column temperature: 40° C.

Flow rate: 0.8 mL/min

Injection volume: 5 μL

Detection Conditions

Detection wavelength: 260 nm

Result of Analysis

Figure 7:
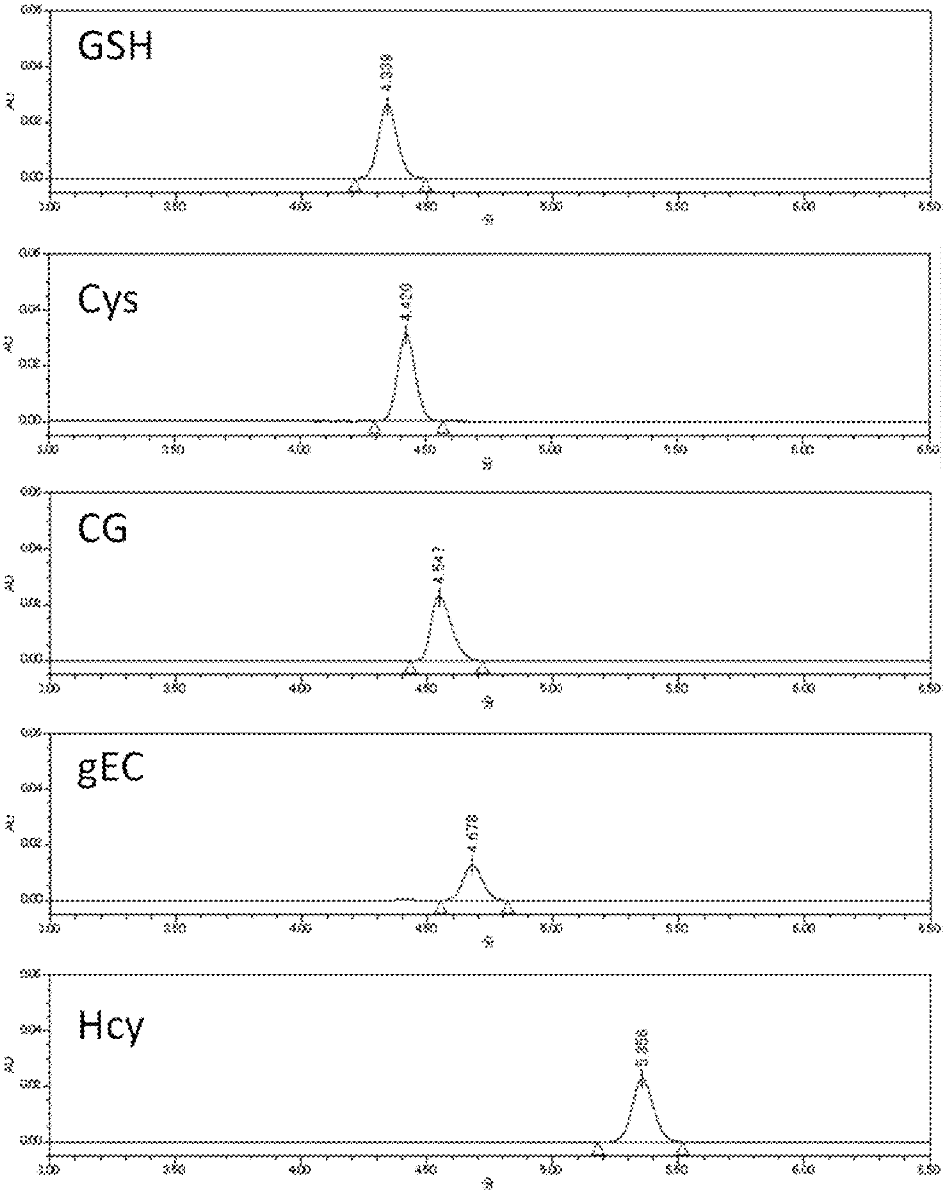
FIG. 7 is a set of exemplary chromatograms of BPSE-derivatized thiols.

The analysis results are listed in the table below. An exemplary chromatogram is illustrated in FIG. 7. FIG. 7 is a set of exemplary chromatograms of BPSE-derivatized thiols.

TABLE 9

| Compound | Retention time (min) | Peak area (μV × sec) |
|---|---|---|
| Cys | 4.420 | 1.56E+5 |
| GSH | 4.339 | 1.38E+5 |
| Hcy | 5.356 | 1.35E+5 |
| CG | 4.547 | 1.31E+5 |
| gEC | 4.678 | 7.07E+4 |

The results indicate that thiols can be derivatized with BPSE under acidic conditions, and that the derivatives can be separated by column chromatography and detected with a UV detector.

Amino acids having sulfanyl are converted into highly hydrophobic amino acids by the derivatization. It is expected that such derivatives can be detected by being favorably separated from other amino acids having low hydrophobicity by column chromatography using an ODS (C18) column.

Example B2 Separation and Detection of Chiral Thiols

In this Example, it is demonstrated that chiral thiols can be derivatized with BPSE and can be detected by being separated by column chromatography using a chiral column.

B2-1. Production of Derivatives

A D,L-cysteine mixed standard solution containing 5 mmol/L of each of L-Cys and D-Cys (manufactured by Sigma) was prepared using 0.1 mol/L hydrochloric acid. To 60 μL of a 20 mmol/L sodium phosphate buffer solution (pH 2.5), 10 μL of the standard thiol solution was added, 10 μL of a BPSE acetonitrile solution (10 mg/mL) was added, and the mixture was stirred and was allowed to stand at room temperature for 10 minutes. Then, 420 μL of a 20 mmol/L sodium phosphate buffer solution (pH 2.5) was added, and the mixture was stirred sufficiently. Furthermore, this solution was diluted ten times with a mobile phase. A sample solution was thus prepared.

B2-2. Analysis of Derivatives

The sample solution was analyzed by LC under the following conditions. Peaks were detected with an HPLC-UV detector.

LC Conditions

Mobile phase: A solution in which formic acid and diethylamine are added in methanol/acetonitrile/water (49/49/2 (v/v/v)) so that the concentrations of formic acid and diethylamine would be 50 mmol/L and 25 mmol/L, respectively, was used under isocratic conditions.

Column: CHIRAL PAK (registered trademark) ZWIX, 3 μm, 150×3 mm (manufactured by Daicel Corporation)

Column temperature: 25° C.

Flow rate: 0.4 mL/min

Injection volume: 10 μL

Detection Conditions

Detection wavelength: 260 nm

Results of Analysis

Figure 8:
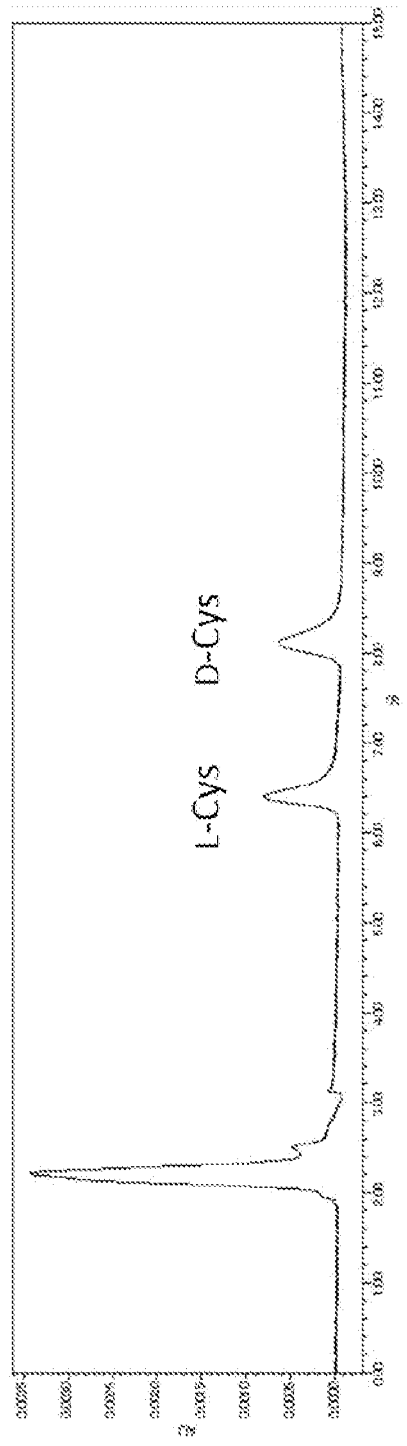
FIG. 8 is an exemplary chromatogram of derivatized chiral thiols.
Figure 9:
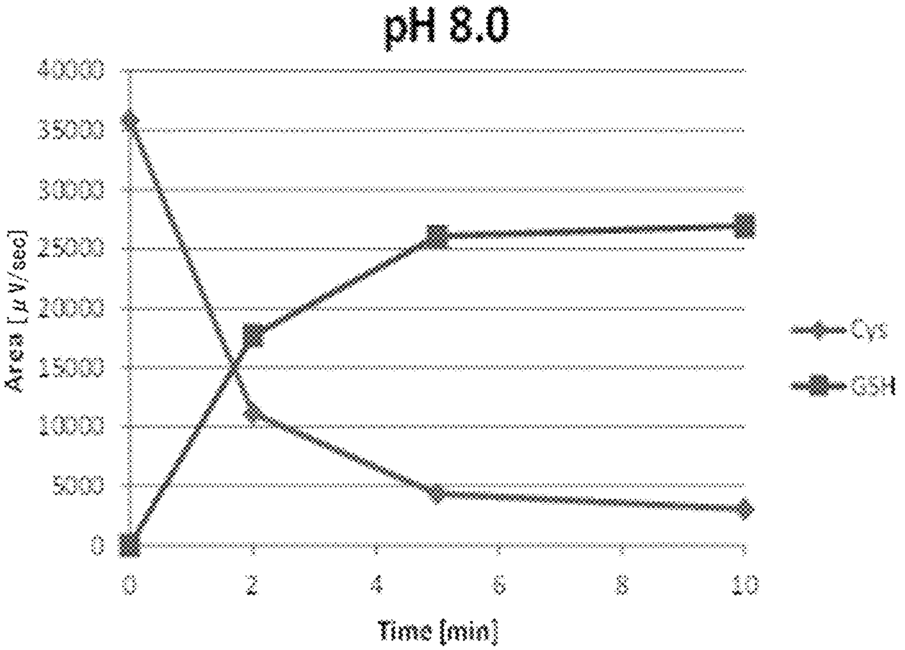
FIG. 9 is a graph illustrating temporal changes in peak area of Cys and GSH at pH 8.0.
Figure 10:
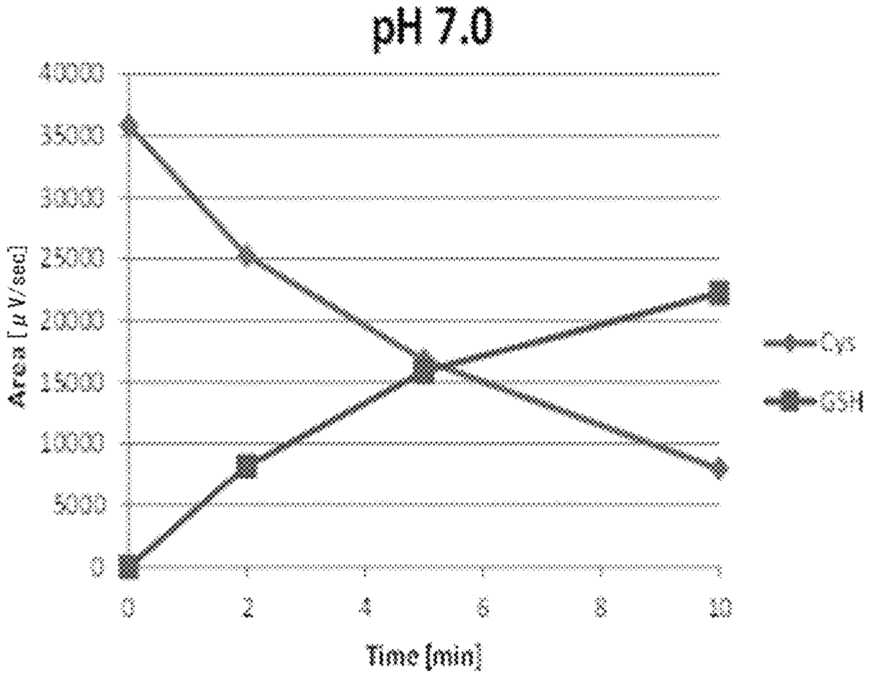
FIG. 10 is a graph illustrating temporal changes in the peak area of Cys and GSH at pH 7.0.
Figure 11:
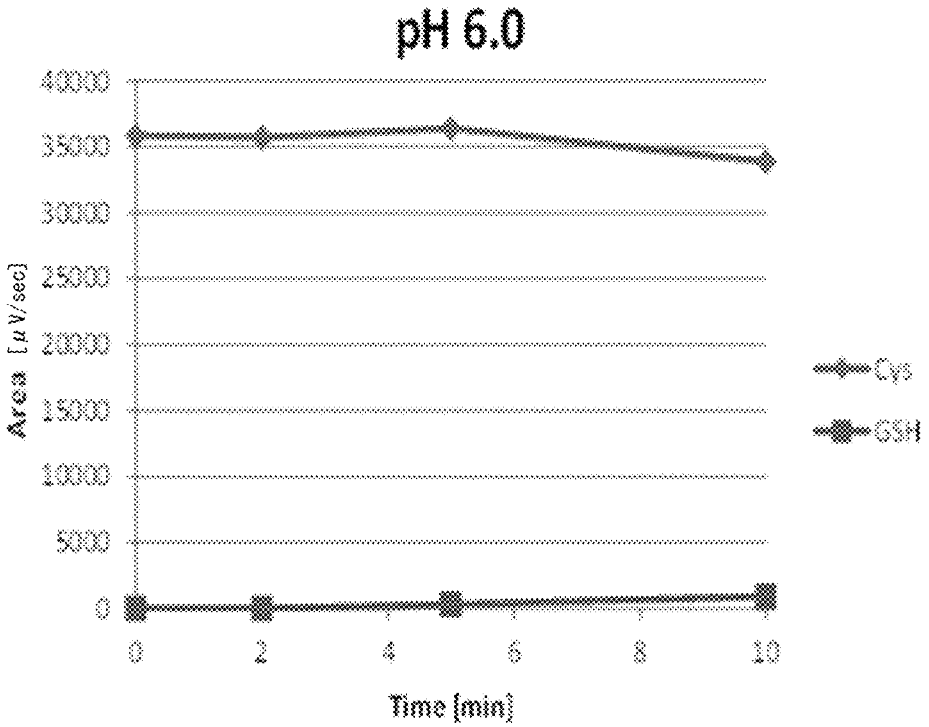
FIG. 11 is a graph illustrating temporal changes in the peak area of Cys and GSH at pH 6.0.
Figure 12:
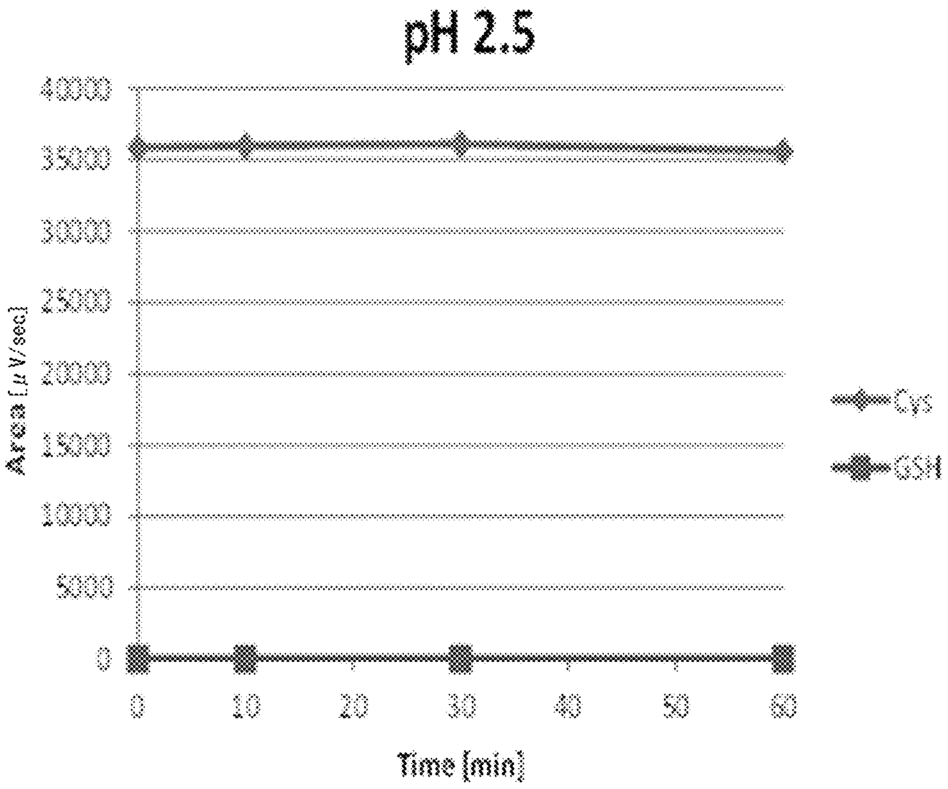
FIG. 12 is a graph illustrating temporal changes in the peak area of Cys and GSH at pH 2.5.

The analysis results are listed in the table below. An exemplary chromatogram is illustrated in FIG. 8. FIG. 8 is an exemplary chromatogram of derivatized chiral thiols.

TABLE 10

| Compound | Retention time (min) | Peak area (μV × sec) |
|---|---|---|
| L-Cys | 6.396 | 1.14E+4 |
| D-Cys | 8.107 | 1.16E+4 |

The results indicate that chiral thiols can be derivatized with BPSE under acidic conditions, and can be detected by being separated with a chiral column. Thus, it has been demonstrated that D-Cys that is scarce in nature can be separated from L-Cys and detected efficiently by the method of this Example.

Example and Reference Example C: Evaluation of Reactivity of Olefin Compounds In this Example and Reference Example, the reactivity of olefin compounds (derivatizing agents) including EMM and BPSE with Cys was evaluated.

The olefin compounds used in this Example and Reference Example and their abbreviations are illustrated below.

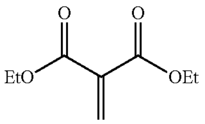
EMM

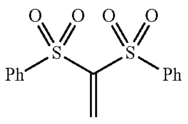
BPSE

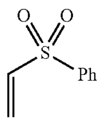
PVS

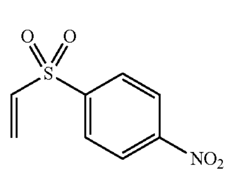
PVS-NO2

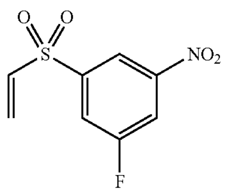
PVS-NO2F

-continued

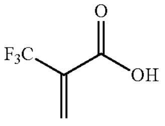
Acry-CP3A

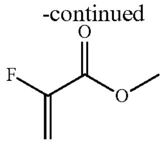
Acry-FE

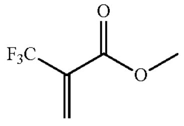
Acry-CF3E

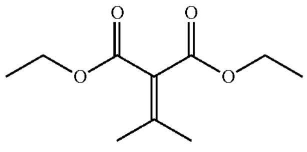
EiPrM

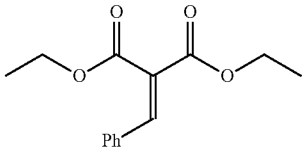
EBzM

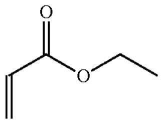
EA

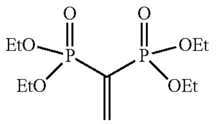
BEPE

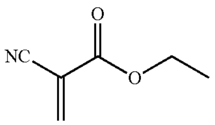
CA

C-1. Preparation of samples and production of Derivatives

L-Cys hydrochloride monohydrate was dissolved into 0.01 mol/L hydrochloric acid so that the concentration would be 1 mmol/L. To 10 μL of this Cys solution, 60 μL of a buffer solution having a certain pH value and 10 μL of a solution of the derivatizing agent (or acetonitrile) were added. The mixtures were allowed to stand at room temperature for 10 minutes. After the reaction, 920 μL of a 0.1% aqueous formic acid solution was added. Sample solutions were thus prepared.

The acetonitrile solutions of the derivatizing agents had been prepared with a concentration of 10 mg/mL (solid) or 10 μL/mL (liquid). The buffer solutions that were used were sodium phosphate buffer solutions (20 mM) having a pH of 2.5 or 7.0. In the derivatization with EMM, sodium citrate (200 mM) having a pH of 3.25 or 4.25 and a sodium phosphate buffer solution (20 mM) having a pH of 6.0 were further used as buffer solutions.

C-2. Analysis of Derivatives

The sample solutions were analyzed by LC-MS/MS under the following conditions. LC that was used was Agilent 1200 series (manufactured by Agilent), and the tandem mass spectrometer that was used was 3200 QTRAP system (manufactured by Sciex). The measurement was performed in the selective ion monitoring (SIM) mode.

LC Conditions

Mobile phase solution A: 0.1% aqueous formic acid solution

Mobile phase solution B: acetonitrile

Gradient conditions: 10% B (0-1.0 min), 10-90% B (1.0-5.0 min), 90% B (5.0-6.5 min), 90-10% B (6.5-7.0 min), and 10% B (7.0-10.0 min)

Column: L-Column ODS, 3 μm, 2.1×50 mm (manufactured by Chemicals Evaluation and Research Institute, Japan)

Column temperature: 40° C.

Flow rate: 0.4 mL/min

Injection volume: 10 μL

MS Conditions

The analysis was performed under the following conditions.

DP (V): 46 EP (V): 8 CEP (V): 14

The table below lists the detection conditions and the retention times of Cys and the Cys derivatives obtained with the derivatizing agents. In the table below, X-Cys means that Cys is derivatized with the derivatizing agent X.

In the detection of EBzM-Cys, two diastereomeric peaks were observed, the respective retention times being listed in the table below.

TABLE 11

| Compound | Time(ms) | Q1 (Da) | Retention time (min) |
|---|---|---|---|
| Cys (underivatized) | 10 | 122.1 | 0.37 |
| EMM-Cys | 10 | 294.1 | 2.42 |
| BPSE-Cys | 10 | 430.1 | 4.22 |
| PVS-Cys | 10 | 290.1 | 1.14 |
| PVS-NO2-Cys | 10 | 335.1 | 2.05 |
| PVS-NO2F-Cys | 10 | 353.1 | 2.69 |
| Acry-CF3A-Cys | 10 | 262.1 | 0.54 |
| Acry-FE-Cys | 10 | 226.1 | 0.49 |
| Acry-CF3E-Cys | 10 | 276.1 | 1.29 |
| EiPrM-Cys | 10 | 322.1 | 3.96 |
| EBzM-Cys | 10 | 370.1 | 4.40, 4.47 |
| EA-Cys | 10 | 222.1 | 0.66 |
| BEPE-Cys | 10 | 422.1 | 3.52 |
| CA-Cys | 10 | 247.1 | 0.69 |

Results of Analysis

The analysis results are listed in the table below. The Cys reaction ratio was calculated using the equation (1) described hereinabove. Items marked with "*" indicate that no data is available.

TABLE 12

| Deriva-tizing | Underivatized Cys peak area (count) | | Reaction ratio | | Derivative peak area (count) | |
|---|---|---|---|---|---|---|
| agents used | pH 2.5 | pH 7.0 | pH 2.5 | pH 7.0 | pH 2.5 | pH 7.0 |
| None (un-derivatized Cys) | 3.8E+05 | —* | — | — | — | — |
| EMM | 2.5E+04 | 1.7E+04 | 93% | 95% | 9.6E+06 | 1.4E+05 |
| BPSE | 1.9E+04 | 9.1E+03 | 95% | 98% | 1.9E+07 | 7.2E+06 |
| PVS | 3.7E+05 | 1.2E+04 | 0.3% | 97% | 1.1E+04 | 8.1E+06 |
| PVS-NO2 | 3.5E+05 | 1.8E+04 | 7.6% | 95% | 7.8E+04 | 5.0E+06 |
| PVS-NO2F | 3.9E+05 | 1.8E+04 | 0% | 95% | 1.1E+05 | 6.3E+06 |
| Acry-CF3A | 1.2E+05 | 4.2E+04 | 67% | 89% | 2.6E+06 | 2.0E+06 |
| Acry-FE | 3.8E+05 | 1.6E+05 | 0% | 57% | 0.0E+00 | 6.3E+05 |
| Acry-CF3E | 1.2E+05 | 9.6E+03 | 68% | 97% | 6.6E+06 | 3.3E+06 |
| EiPrM | 3.5E+05 | 1.8E+05 | 6.9% | 52% | 0.0E+00 | 8.0E+05 |
| EBzM | 3.5E+05 | 2.1E+04 | 7.9% | 94% | 2.0E+04 | 1.9E+07 |
| EA | 3.2E+05 | 3.4E+04 | 14% | 91% | 0.0E+00 | 5.4E+06 |
| BEPE | 2.0E+04 | 1.3E+04 | 95% | 97% | 3.6E+07 | 3.3E+07 |
| CA | 1.1E+04 | —* | 97% | —* | 3.0E+06 | —* |

At pH 7.0, derivatization occurred with all the agents, and the derivatives were detected. Under the acidic conditions at pH 2.5, derivatives were formed when an olefin compound including an ethylene structure with two electron-withdrawing groups (EMM, BPSE, Acry-CF3A, Acry-MFE, EiPrM, EBzM, BEPE, CA) was used. In particular, derivatives were formed with a high reaction ratio when an olefin compound represented by the formula (I) (EMM, BPSE, Acry-CF3A, Acry-CF3E, BEPE, CA) was used.

The table below lists the results of the reaction in various buffer solutions using EMM as the derivatizing agent.

TABLE 13

| Reaction conditions | Residual Cys (count) | Reaction ratio | Derivatized Cys peak (count) |
|---|---|---|---|
| pH 2.5 Na phosphate buffer solution | 2.5E+04 | 93% | 9.6E+06 |
| pH 3.25 Na citrate buffer solution | 1.2E+04 | 97% | 9.2E+06 |
| pH 4.25 Na citrate buffer solution | 1.6E+04 | 96% | 8.4E+06 |
| pH 6.0 Na phosphate buffer solution | 1.9E+04 | 95% | 2.4E+06 |
| pH 7.0 Na phosphate buffer solution | 1.7E+04 | 95% | 1.4E+05 |

The results indicate that the peak area of the derivatized Cys decreases when the pH is 6.0 or more.

Reference Example D: Behavior of Organic Substances Under Various pH Conditions In this Reference Example, the stability of organic substances under acidic conditions is evaluated by observing the behavior of the organic substances under various pH conditions.

D-1. Observation of Thiol Exchange Reaction

Preparation of Samples

L-Cys hydrochloride monohydrate and GSSG were separately dissolved into 0.01 mol/L hydrochloric acid so that the concentrations would be 10 mmol/L and 50 mmol/L, respectively. To 50 μL of the Cys solution (10 mmol/L), 850 μL of a sodium phosphate buffer solution (pH 2.5, 6.0, 7.0 or 8.0) and 100 μL of the GSSG solution (50 mmol/L) were added. Mixed solutions were thus prepared. (The final solutions contained 0.5 mmol/L of Cys and 5 mmol/L of GSSG.) The solutions were sampled over time, and derivatization was performed with BPSE. The samples were analyzed by LC under the following conditions, and the area values of Cys and GSH were measured. The peaks were detected with an HPLC-UV detector.

Sampling and Derivatization

To 10 μL of each of the mixed solutions, 10 μL of a 10% (w/v) aqueous trichloroacetic acid solution, 80 μL of a pH 2.5 sodium phosphate buffer solution and 20 μL of a BPSE acetonitrile solution (5 mg/mL) were added. The mixtures were allowed to stand at room temperature for 10 minutes. After the reaction, 100 μL of a pH 2.5 sodium phosphate buffer solution was added. Sample solutions were thus prepared.

LC Conditions

Mobile phase solution A: 20 mmol/L sodium phosphate buffer solution (pH 2.5)

Mobile phase solution B: acetonitrile

Gradient conditions: 25% B (0-8.0 min), 25-90% B (8.0-9.0 min), 90% B (9.0-11.0 min), 90-25% B (11.0-12.0 min), and 25% B (12.0-15.0 min)

Column: Triart C18, 3 μm, 150×4.6 mm (manufactured by YMC)

Column temperature: 40° C.

Flow rate: 1.0 mL/min

Injection volume: 10 μL

Under the above conditions, Cys is eluted in 6.3 minutes and GSH in 6.8 minutes.

Detection Conditions

Detection wavelength: 260 nm

Results of Analysis

The analysis results are listed in the tables below and illustrated in FIGS. 9 to 12. FIGS. 9, 10, 11 and 12 are graphs illustrating temporal changes in the peak area of Cys and GSH at pH 8.0, pH 7.0, pH 6.0 and pH 2.5, respectively. The data at 0 minute in the cases of pH 6.0, pH 7.0 and pH 8.0 were taken as data without buffer solution treatment, and were equated with the data at 0 minute in the case of pH 2.5.

TABLE 14

| pH 8.0 | | |
|---|---|---|
| Time[min] | Cys[μV/sec] | GS[μV/sec] |
| 0 | 35846 | 0 |
| 2 | 11145 | 17721 |
| 5 | 4330 | 26086 |
| 10 | 3018 | 26965 |

TABLE 15

| pH 7.0 | | |
|---|---|---|
| Time[min] | Cys[μV/sec] | GSH[μV/sec] |
| 0 | 35846 | 0 |
| 2 | 25265 | 8180 |
| 5 | 16777 | 15833 |
| 10 | 7968 | 22246 |

TABLE 16

| pH 6.0 | | |
|---|---|---|
| Time[min] | Cys[μV/sec] | GSH[μV/sec] |
| 0 | 35846 | 0 |
| 2 | 35713 | 0 |
| 5 | 36387 | 317 |
| 10 | 33875 | 911 |

TABLE 17

| pH 2.5 | | |
|---|---|---|
| Time[min] | Cys[μV/sec] | GSH[μV/sec] |
| 0 | 35846 | 0 |
| 10 | 35988 | 0 |
| 30 | 36121 | 0 |
| 60 | 35613 | 0 |

The results indicate that Cys and GSSG react quickly at a pH of 7.0 or more, and that GSH resulting from the exchange reaction is detected while the amount of Cys decreases.

On the other hand, the reaction between Cys and GSSG hardly proceeds at a pH of 6.0 or less. At a pH of 2.5, in particular, GSH as a product of the exchange reaction is not detected even after the lapse of 1 hour.

The above results indicate that even when a sample contains a disulfide compound and a thiol compound, the thiol compound can be accurately analyzed under acidic conditions.

D-2. Observation of Thiol Oxidation Reaction

Preparation of Samples

L-Cys hydrochloride monohydrate and copper sulfate pentahydrate were separately dissolved into 0.01 mol/L hydrochloric acid so that the concentrations would be 10 mmol/L and 0.1 mmol/L, respectively. To 50 μL of the Cys solution (10 mmol/L), 850 μL of a sodium phosphate buffer solution (pH 2.5, 6.0, 7.0 or 8.0) and 100 μL of the aqueous copper sulfate solution (0.1 mmol/L) were added. Mixed solutions were thus prepared. (The final solutions contained 0.5 mmol/L of Cys and 0.01 mmol/L of copper sulfate.) The solutions were sampled over time, and derivatization was performed with BPSE. The samples were analyzed by LC under the same conditions as in (D-1. Observation of thiol exchange reaction), and the area values of Cys were measured. The same analysis method and the derivatization method as those in (D-1. Observation of thiol exchange reaction) were used.

Results of Analysis

Figure 13:
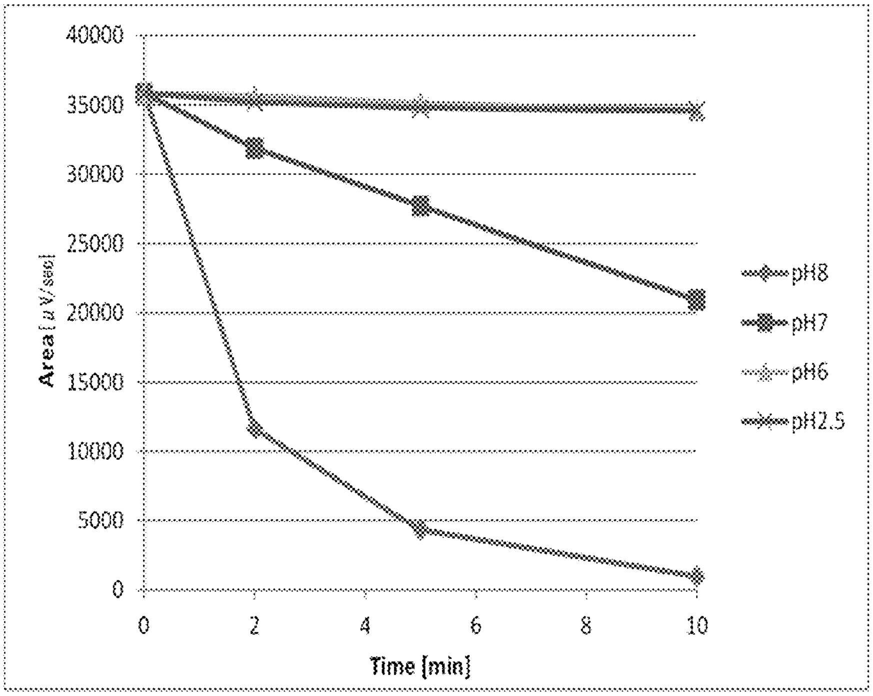
FIG. 13 is a graph illustrating temporal changes in the peak area of Cys at pH 8.0, pH 7.0, pH 6.0 and pH 2.5.

The analysis results are listed in the table below and illustrated in FIG. 13. FIG. 13 is a graph illustrating temporal changes in the peak area of Cys at pH 8.0, pH 7.0, pH 6.0 and pH 2.5. The data at 0 minute in the cases of pH 6.0, pH 7.0 and pH 8.0 were taken as data without buffer solution treatment, and were equated with the data at 0 minute in the case of pH 2.5.

TABLE 18

| Time [min] | pH 2.5 [μV/sec] | pH 6.0 [μV/sec] | pH 7.0 [μV/sec] | pH 8.0 [μV/sec] |
|---|---|---|---|---|
| 0 | 35846 | 35846 | 35846 | 35846 |
| 2 | 35210 | 35633 | 31874 | 11620 |
| 5 | 34788 | 35110 | 27711 | 4330 |
| 10 | 34580 | 34576 | 20929 | 965 |

The results indicate that at a pH of 7 or more, Cys is rapidly decreased and Cys is quickly oxidized.

On the other hand, there is little decrease in Cys at a pH of 6.0 or less, indicating that the oxidation reaction of Cys proceeds hardly.

The above results indicate that the oxidation reaction of a thiol compound is suppressed under acidic conditions, and that the thiol compound can be analyzed accurately.

Example E Derivatization of Sulfanyl Groups and Amino Groups

In this Example, it has been demonstrated that when cysteine or cystine is mixed together with EMM under acidic conditions and thereafter the solution is adjusted to a basic pH, the cysteine or cystine is derivatized by the reaction of the amino group(s) ($—NH_2$) in cysteine or cystine with EMM.

Specifically, a derivative was obtained by a series of reactions in which the sulfanyl group (—SH) in cysteine reacted with EMM under acidic conditions and was thereby converted into a substituent that was stable to oxidation, and thereafter the amino group in cysteine reacted with EMM under basic conditions.

Under acidic conditions, amino groups usually do not react with EMM. Therefore, a disulfide compound having amino groups and no sulfanyl groups, such as cystine, usually does not react with EMM under acidic conditions and thus is not derivatized. However, it has been demonstrated that even such a disulfide compound is derivatized under basic conditions by the reaction of the amino groups with EMM.

By performing reaction not only between a sulfanyl group and EMM but also between an amino group and EMM, a disulfide compound that is not derivatized under acidic conditions attains high hydrophobicity and thus can be separated easily by liquid chromatography. Furthermore, such a derivative can be detected with a mass spectrometer with increased sensitivity.

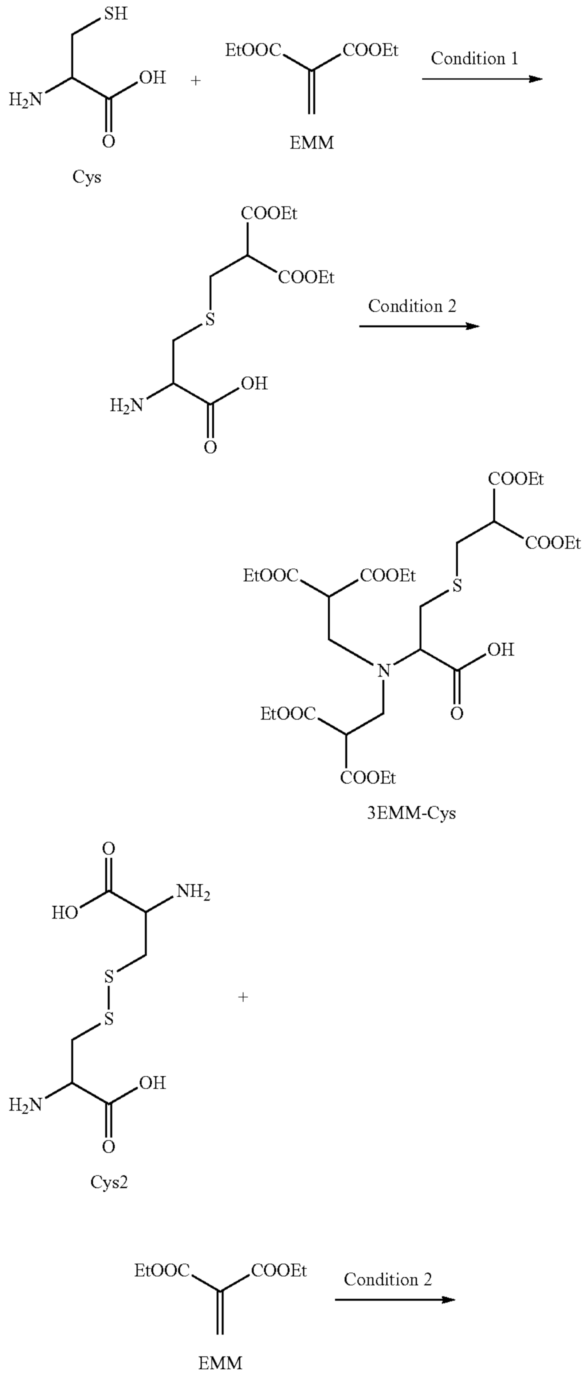

Cys

EMM

3EMM-Cys

Cys2

EMM

-continued

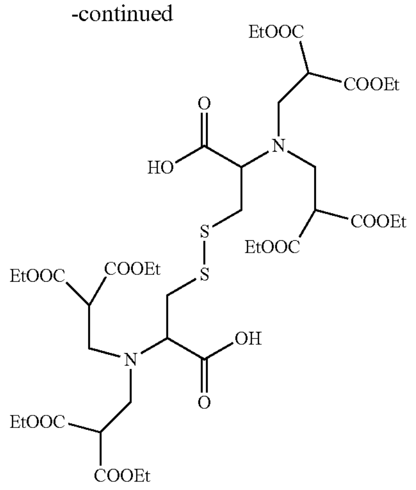

4EMM-Cys2

Condition 1: Acidic conditions Condition 2: Weakly basic conditions

E-1. Production of Derivatives

Cysteine or cystine (manufactured by Sigma) was dissolved into 0.01 mol/L hydrochloric acid so that the concentration would be 250 μmol/L. Standards were thus prepared. To 20 μL of the standard, 20 μL of a 10% aqueous trichloroacetic acid solution and 40 μL of 0.1 mol/L hydrochloric acid were mixed together, and the mixture was stirred sufficiently. With 50 μL of the solution, 300 μL of a 20 mmol/L sodium phosphate buffer solution (pH 2.5) was mixed, and 50 μL of an EMM acetonitrile solution (10 μL/mL) was added. The mixture was stirred and was allowed to stand at 40° C. for 5 minutes. A 100 μL portion of this solution was mixed together with 200 μL of a 100 mmol/L sodium phosphate buffer solution (pH 9.0). The mixture was further stirred and was allowed to stand at 40° C. for 5 minutes. To a 15 μL portion of the solution, 50 μL of a 0.3% formic acid solution was added, and stirred sufficiently. Analysis samples were thus prepared.

E-2. Analysis of Derivatives

The sample solutions were analyzed by LC-MS/MS under the following conditions. LC that was used was Agilent 1290 Infinity II series (manufactured by Agilent), and the tandem mass spectrometer that was used was QTRAP 5500 system (manufactured by Sciex).

LC Conditions

Mobile phase solution A: 0.1% formic acid, mobile phase solution B: acetonitrile Gradient conditions: 30-60% B (0-6.0 min), 60-90% B (6.0-7.5 min), 90% B (7.5-9.0 min), 90-30% B (9.0-9.1 min), and 30% B (9.1-10.0 min)

Column: L-Column ODS, 3 μm, 2.1×50 mm (manufactured by Chemicals Evaluation and Research Institute, Japan) fitted with Inertsil ODS-3, 3 μm, 1.5×10 mm Guard column for UHPLC (manufactured by GL-Science) as a guard column Column temperature: 40° C.

Flow rate: 0.4 mL/min

Injection volume: 1 μL

MS/MS Conditions

The analysis was performed under conditions listed in the table below.

TABLE 19

| Compound | Q1 (Da) | Q3 (Da) | Time (ms) | DP (V) | EP (V) | CE (V) | CXP (V) |
|---|---|---|---|---|---|---|---|
| Cysteine | 638.2 | 173 | 20 | 106 | 10 | 29 | 26 |
| Cystine | 929.2 | 597 | 20 | 76 | 10 | 10 | 20 |

Results of Analysis

The analysis results are listed in the table below. Exemplary chromatograms are illustrated in FIG. 14.

In the table below and in FIG. 14, "3EMM-Cysteine" and "3EMM-Cys" mean derivatives obtained by the reaction of one cysteine molecule with three EMM molecules. "4EMM-Cystine" and "4EMM-Cys2" mean derivatives obtained by the reaction of one cystine molecule with four EMM molecules.

Figure 14:
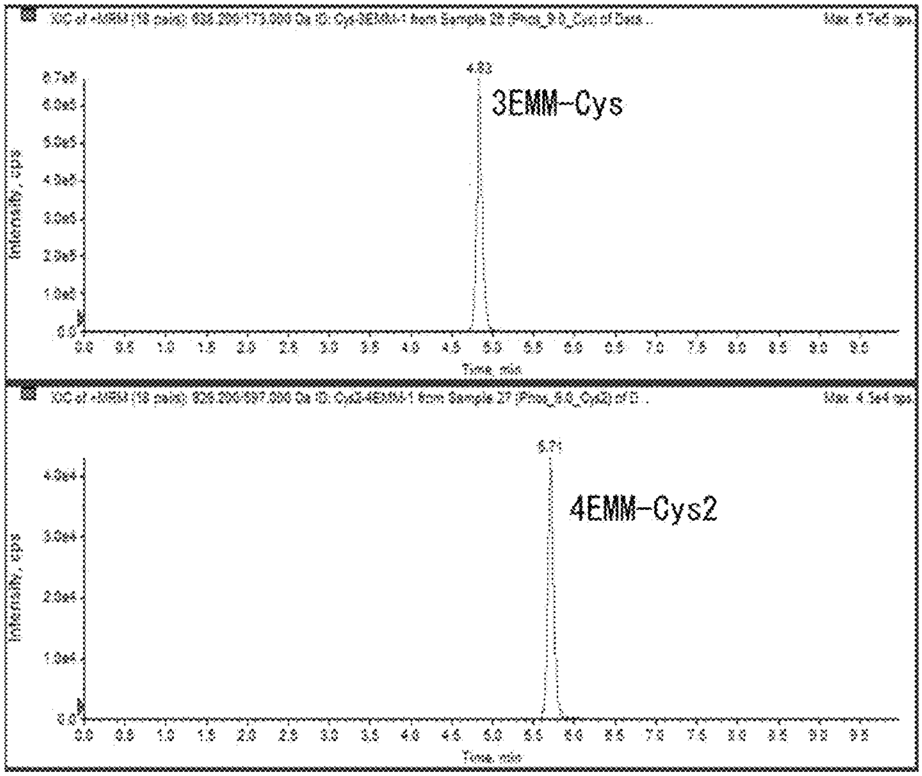
FIG. 14 is a set of exemplary chromatograms illustrating a peak of EMM-derivatized cysteine and a peak of EMM-derivatized cystine.

FIG. 14 is a set of exemplary chromatograms illustrating a peak of EMM-derivatized cysteine and a peak of EMM-derivatized cystine.

TABLE 20

| Compound | Retention time (min) | Peak area (count) |
|---|---|---|
| 3EMM-Cysteine | 4.83 | 3210000 |
| 4EMM-Cystine | 5.71 | 213000 |

The results indicate that cysteine is derivatized by a series of reactions with EMM in which the sulfanyl group reacts with EMM under acidic conditions and, after the solution has been adjusted to a basic pH, the amino group reacts with two molecules of EMM.

In the case of cystine, the derivatization reaction occurred in the basic reaction solution between the two amino groups and four molecules of EMM.

That is, the above results indicate that cysteine and cystine can be analyzed by LC-MS/MS as a compound reacted with three EMM molecules and as a compound reacted with four EMM molecules, respectively.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for analyzing a sample containing an organic substance, comprising:

(1) mixing a sample containing an organic substance containing one or more groups selected from the group consisting of sulfanyl, selanyl and sulfino, and an olefin compound containing an ethylene structure having at least two electron-withdrawing groups except halogen atoms under an acidic condition to form a treated sample containing a derivative of the organic substance; and (2) analyzing the derivative of the organic substance in the treated sample, wherein the olefin compound is N-ethylmaleimide or a compound represented by formula (I):

(I)

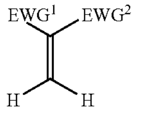

wherein $EWG^1$ and $EWG^2$ each independently represent $—C(=O)—OR^1$, $—S(=O)_2—R^2$, $—P(=O)(—OR^3)_2$, cyano, a halogen atom-substituted alkyl, carboxy, nitro, $—S(=O)—R^4$, $—C(=O)—R^5$ or $—C(=O)—NR^6R^7$, and $EWG^1$ and $EWG^2$ optionally form a ring together with the carbon atom to which $EWG^1$ and $EWG^2$ are bonded, wherein $R^1$, $R^2$, $R^3$ and $R^4$ each independently represent a monovalent hydrocarbon group or a monovalent heterocyclic group and optionally each have a substituent, and $R^5$, $R^6$ and $R^7$ each independently represent a hydrogen atom, a monovalent hydrocarbon group or a monovalent heterocyclic group and optionally each have a substituent.

2. The method for analyzing a sample containing an organic substance according to claim 1, wherein said (2) analyzing comprises:

(2a) separating the derivative of the organic substance from the treated sample, and (2b) detecting the derivative of the organic substance separated.

3. The method for analyzing a sample containing an organic substance according to claim 1, wherein the sample further contains a disulfide compound.

4. The method for analyzing a sample containing an organic substance according to claim 3, wherein the disulfide compound is one or more selected from the group consisting of oxidized glutathione and cystine.

5. The method for analyzing a sample containing an organic substance according to claim 1, wherein the organic substance further contains an amino group, and said (1) mixing comprises (1') mixing the sample with the olefin compound under the acidic condition and subsequently performing mixing under a neutral or basic condition to form a treated sample containing a derivative of the organic substance.

6. The method for analyzing a sample containing an organic substance according to claim 1, wherein the acidic condition is a condition at which pH is less than 6.0.

7. The method for analyzing a sample containing an organic substance according to claim 1, wherein the organic substance is one or more members selected from the group consisting of cysteine, reduced glutathione, γ-glutamylcysteine, cysteinylglycine, homocysteine, N-acetylcysteine, cysteine persulfide, hypotaurine, glutathione persulfide, and a peptidic compound containing a cysteine residue.

8. The method for analyzing a sample containing an organic substance according to claim 1, wherein $EWG^1$ and $EWG^2$ each independently represent $—C(=O)—OR^1$ or $—S(=O)_2—R^2$, wherein $R^1$ and $R^2$ each independently represent a monovalent hydrocarbon group or a monovalent heterocyclic group and optionally each have a substituent.

9. The method for analyzing a sample containing an organic substance according to claim 1, wherein the olefin compound is N-ethylmaleimide, diethyl methylenemalonate, or 1,1-bis(phenylsulfonyl) ethylene.

10. The method for analyzing a sample containing an organic substance according to claim 1, wherein the olefin compound is diethyl methylenemalonate or 1,1-bis(phenylsulfonyl)ethylene, and the organic substance is cysteine.

11. The method for analyzing a sample containing an organic substance according to claim 1, wherein the said mixing (1) is performed at a temperature of 50° C. or lower.

12. The method for analyzing a sample containing an organic substance according to claim 1, wherein the sample is a biological sample or an environmental sample.

13. The method for analyzing a sample containing an organic substance according to claim 1, wherein said mixing (1) under the acidic condition is carried out in an acidic solution, and the acidic solution is an aqueous solution or a solution containing water and an organic solvent wherein a weight percentage of the organic solvent in the solution relative to water is 50 wt % or less.

14. The method for analyzing a sample containing an organic substance according to claim 2, wherein said separating (2a) is performed by hydrophilic interaction liquid chromatography.

* * * * *